Figure 1:
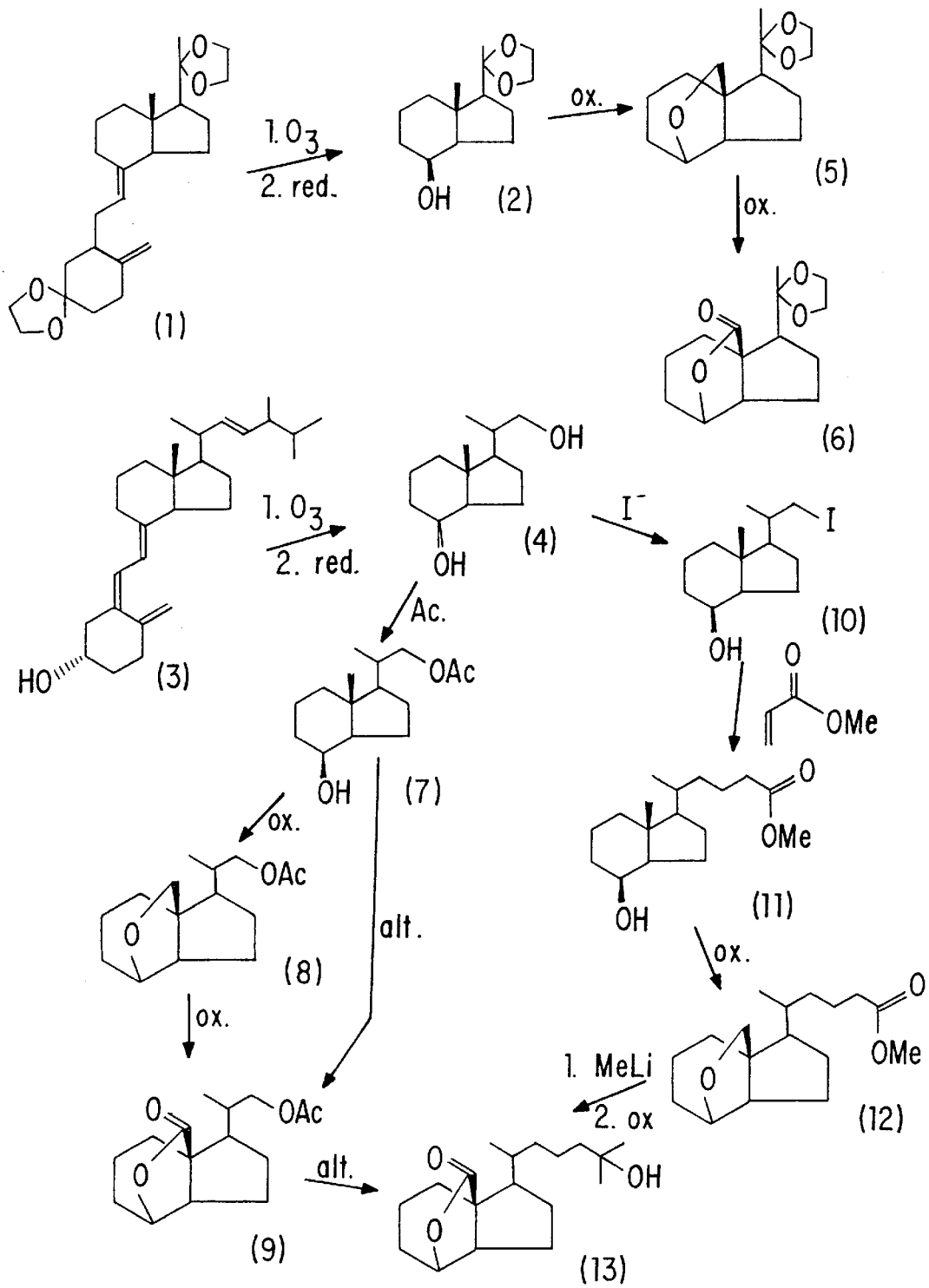
Figure 2:
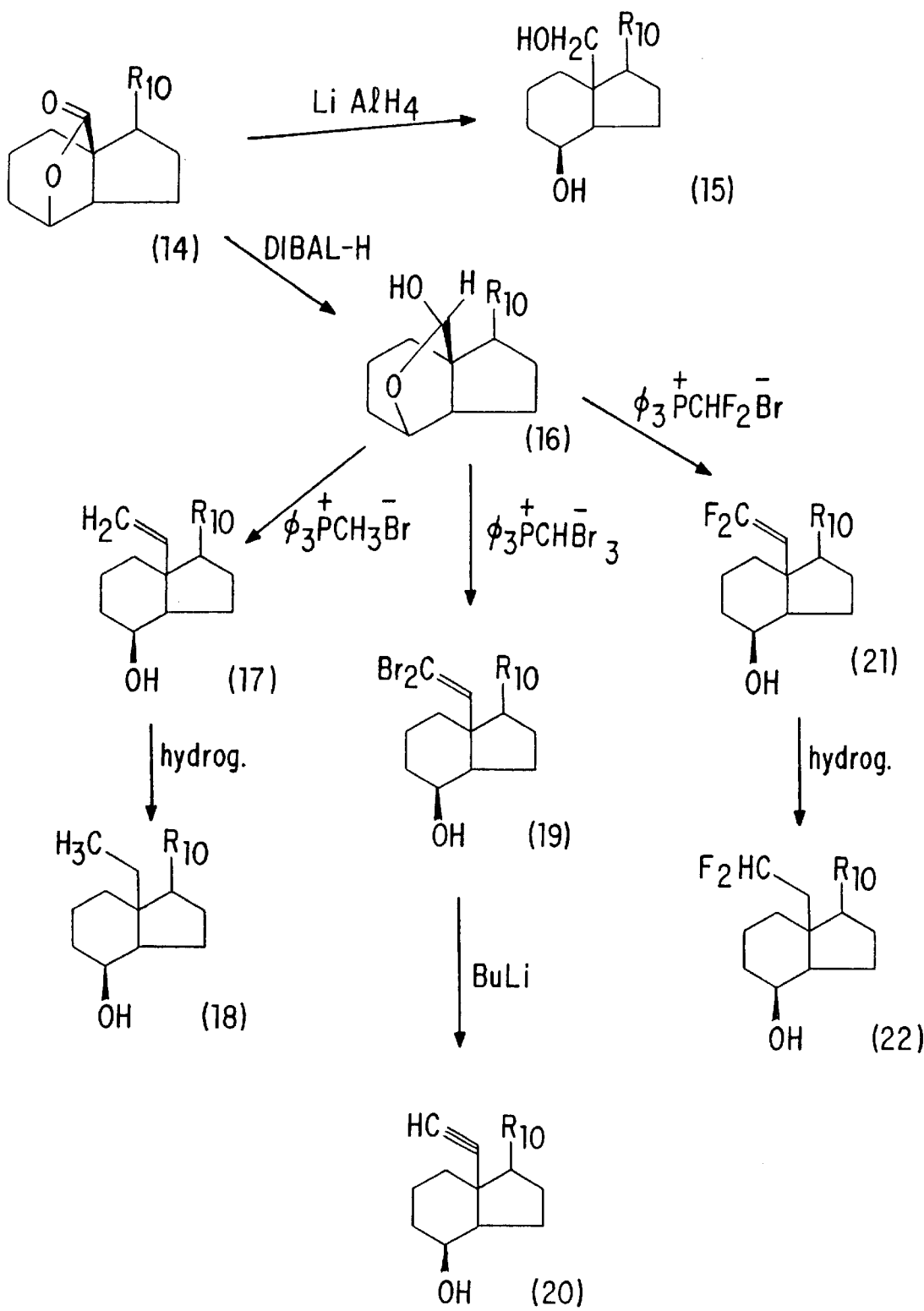
Figure 3:
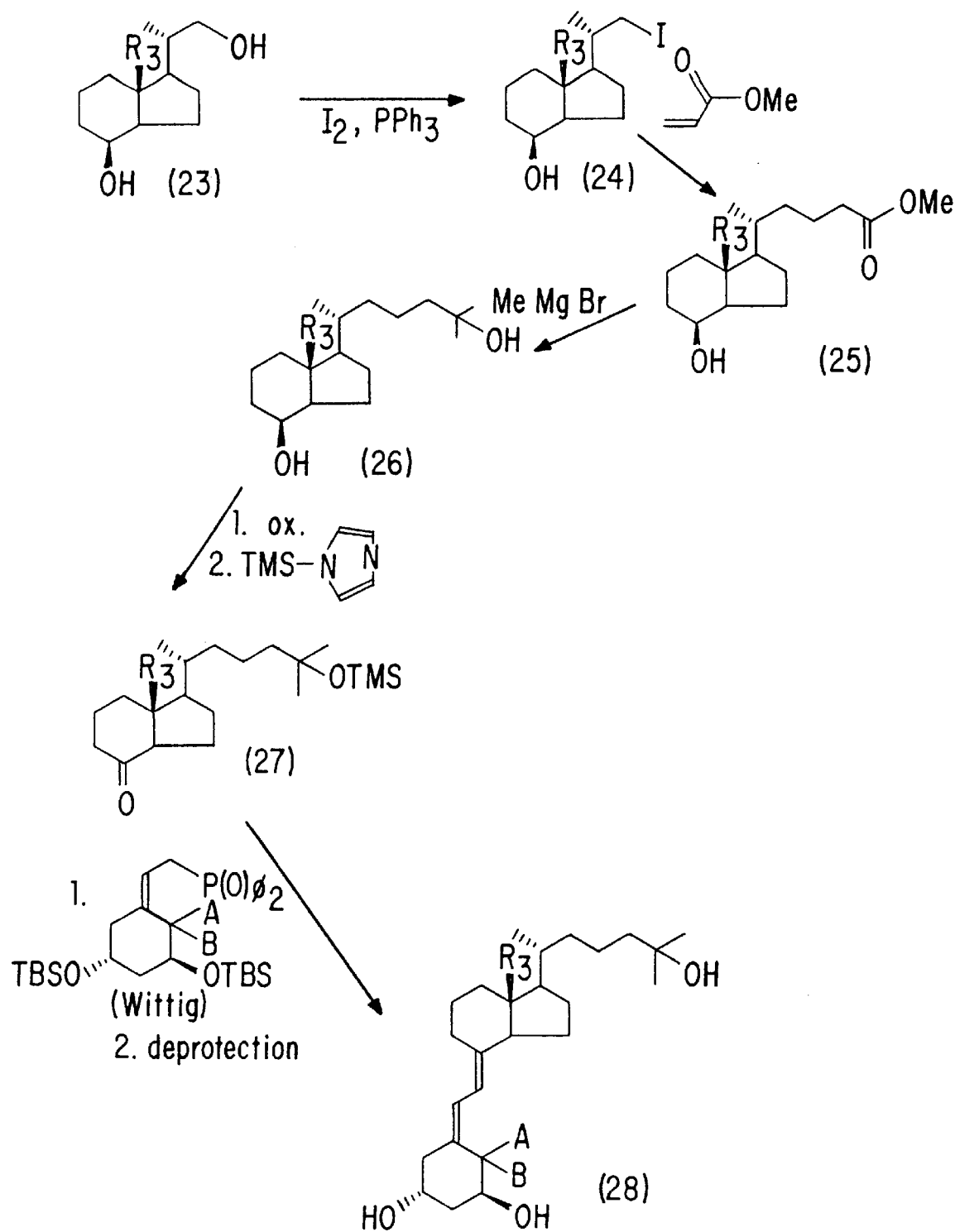
Figure 4:
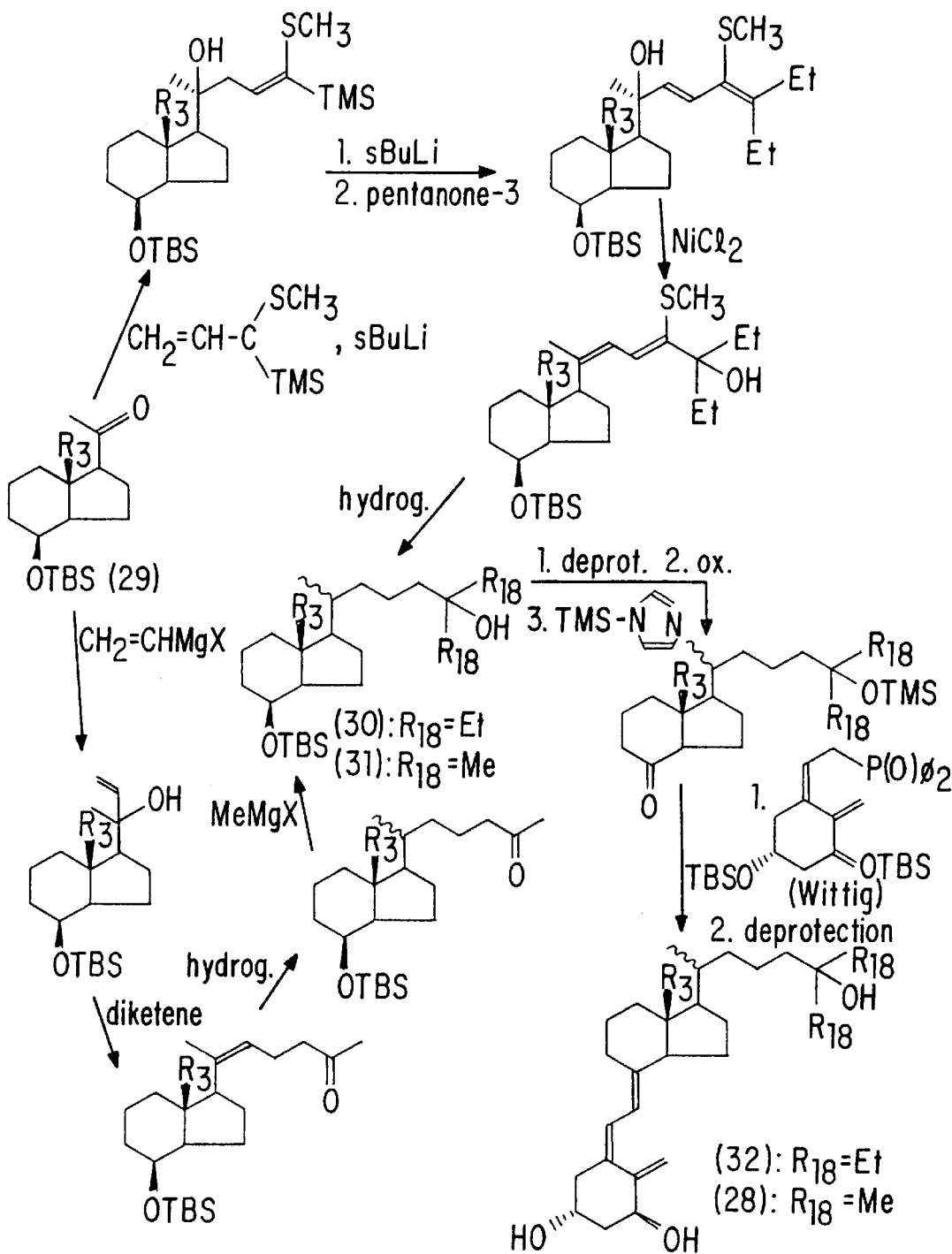
Figure 5:
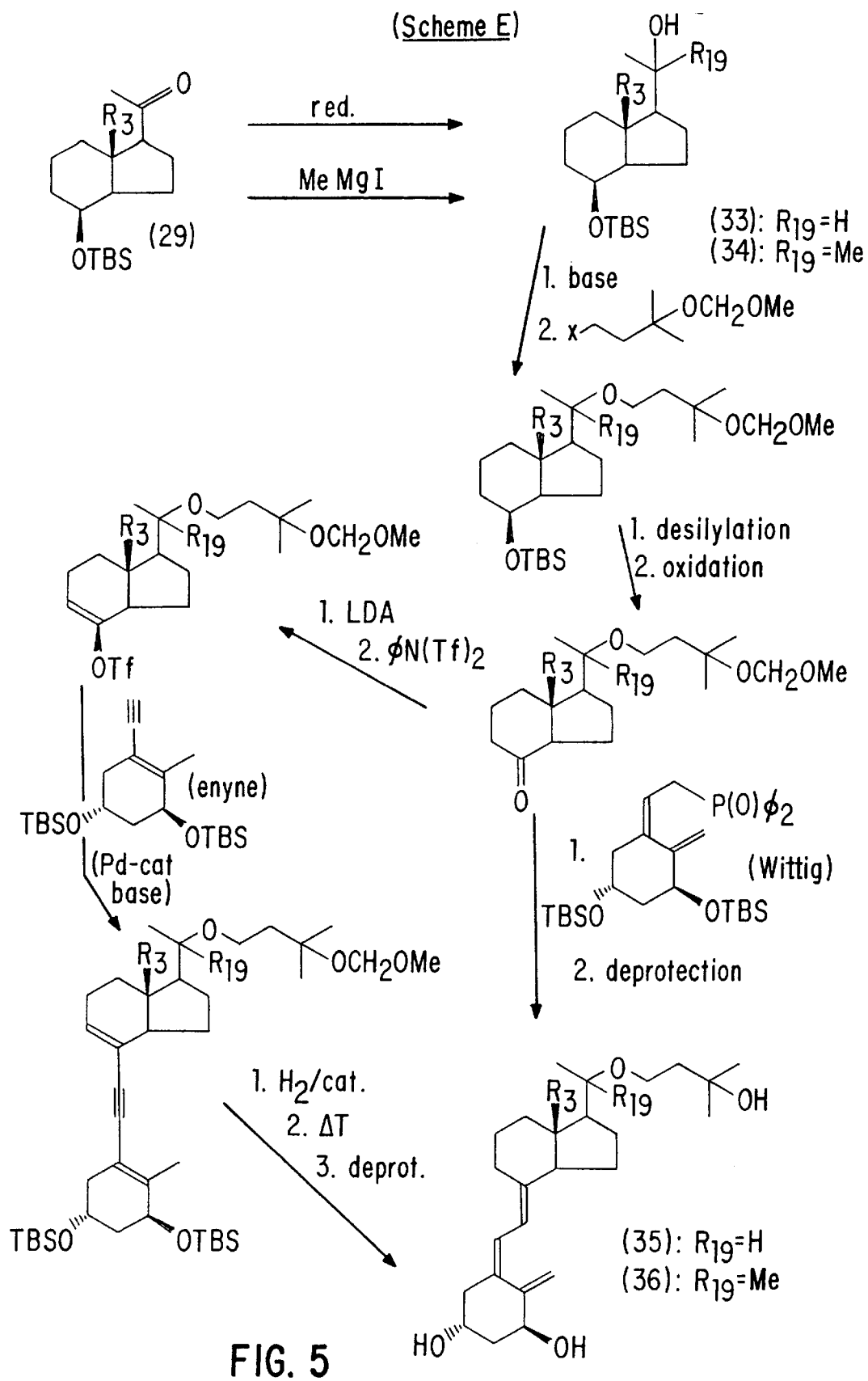
Figure 6:
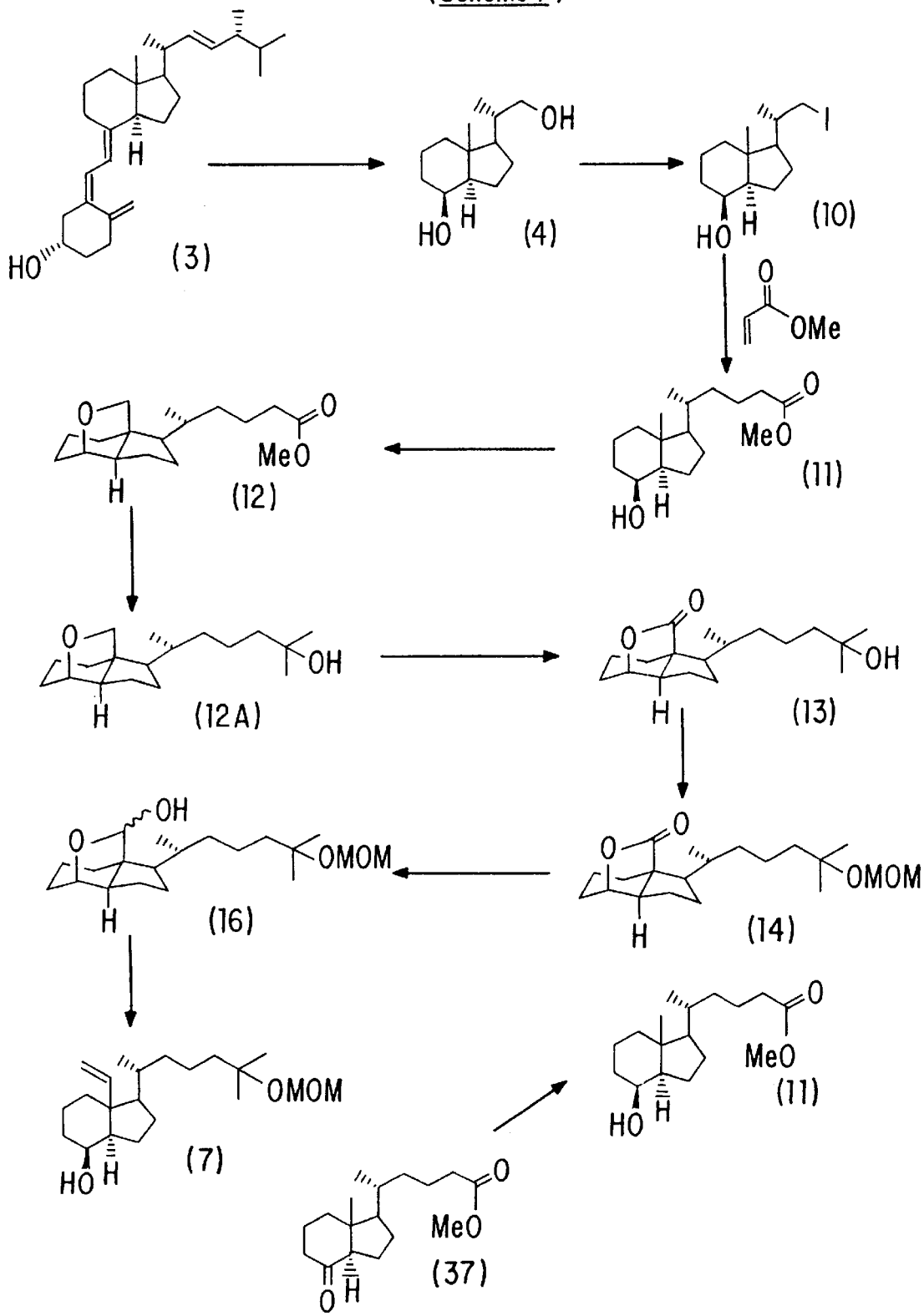
Figure 7:
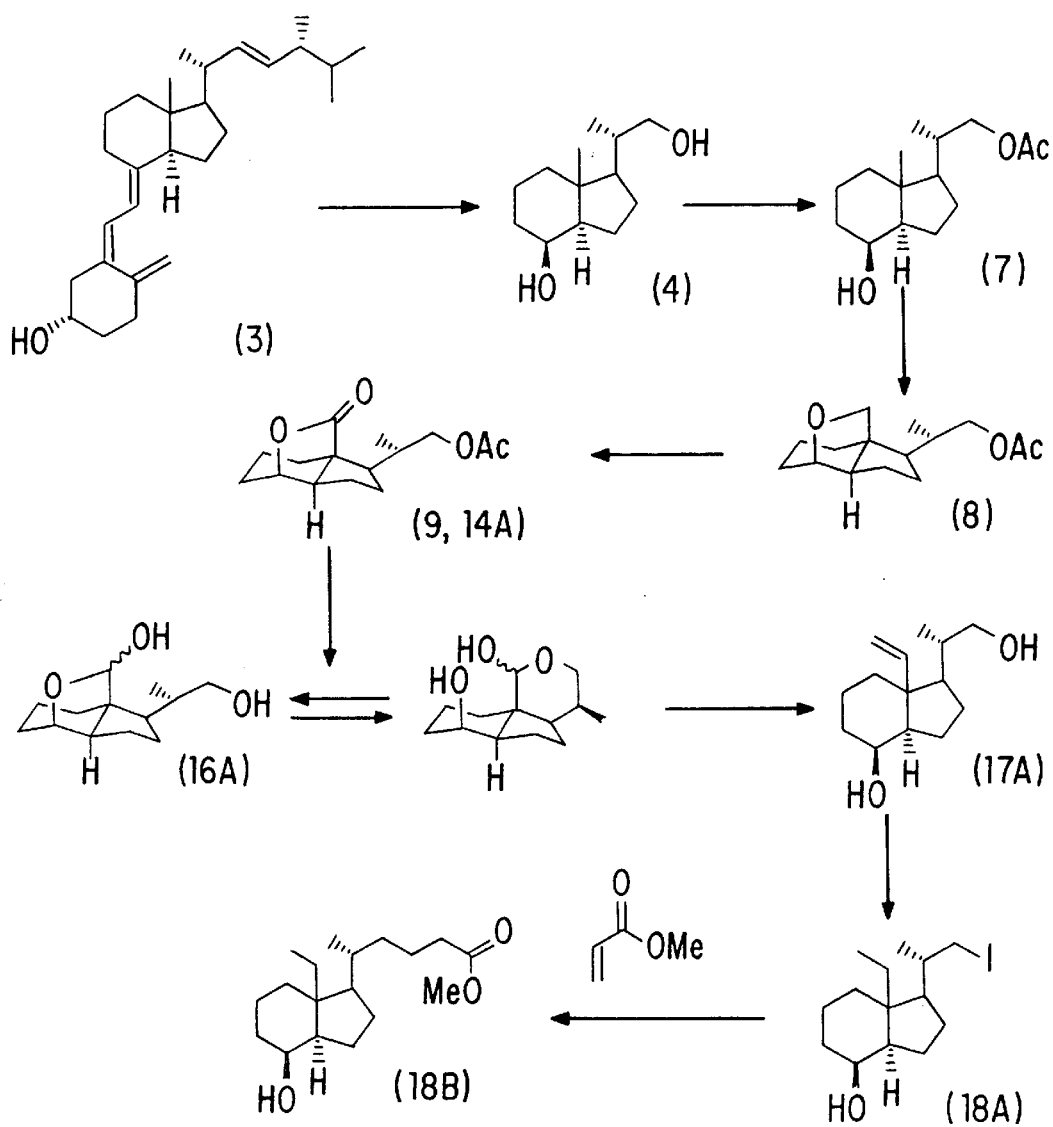
Figure 8:
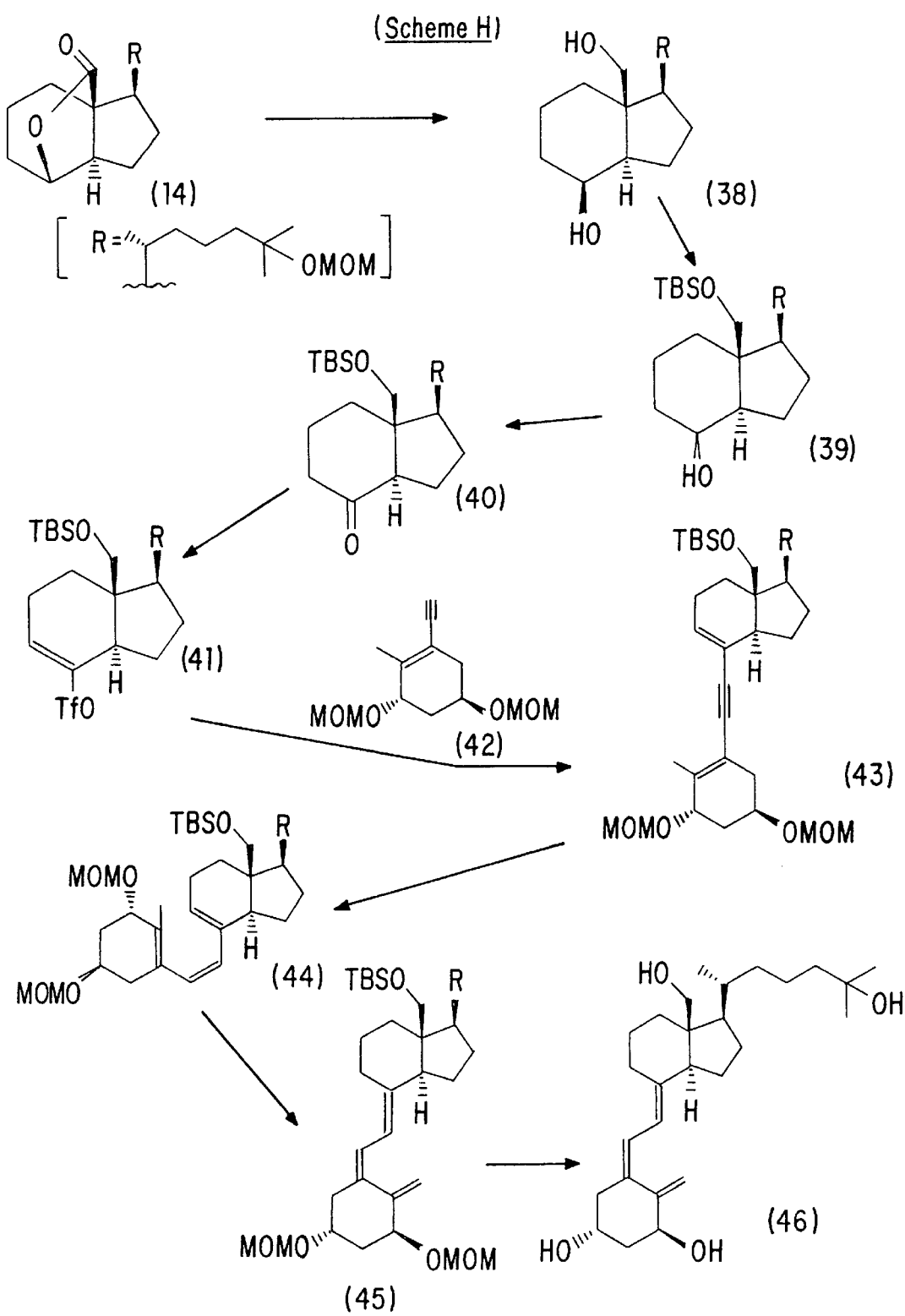
Figure 9:
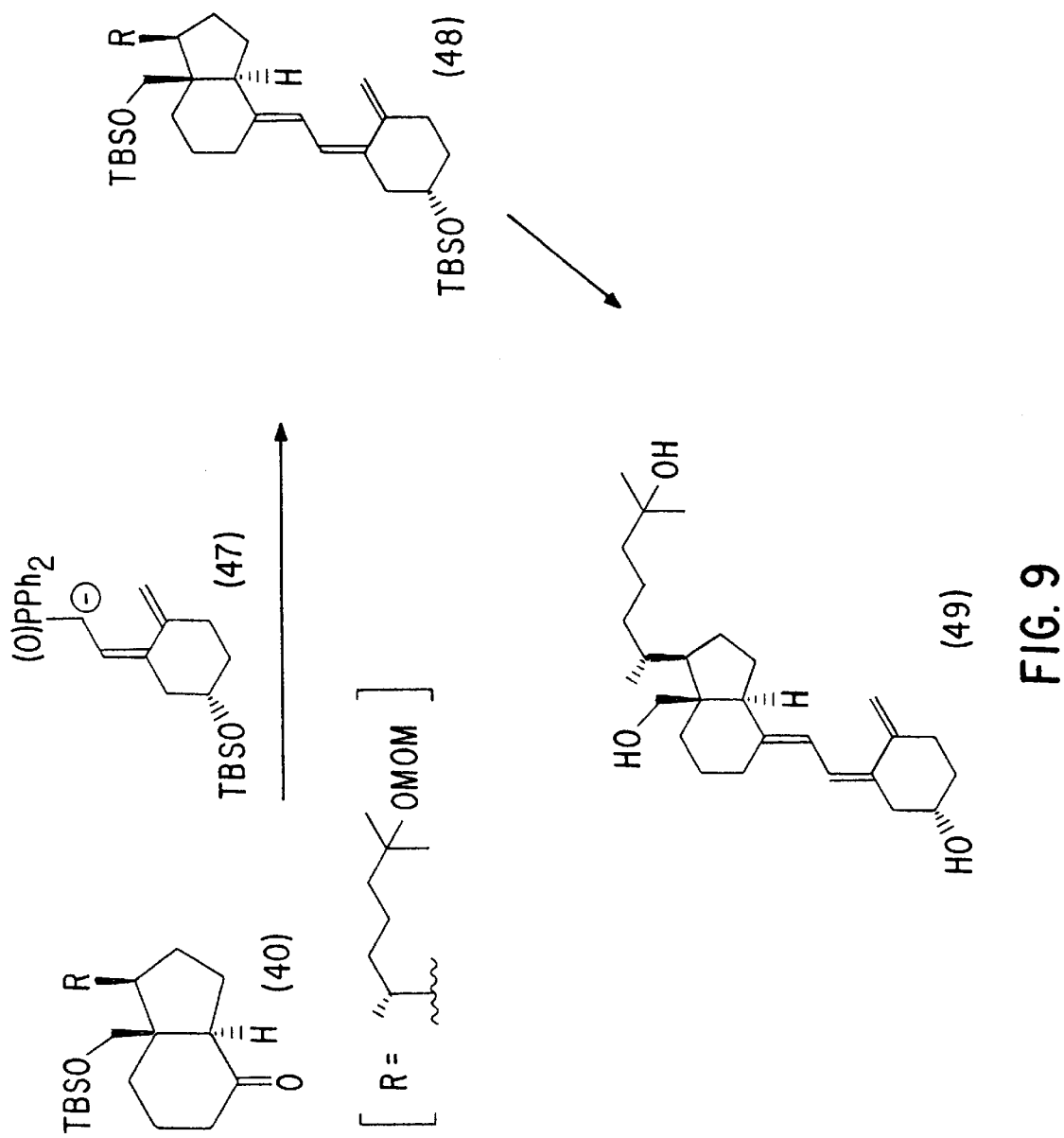
Figure 10:
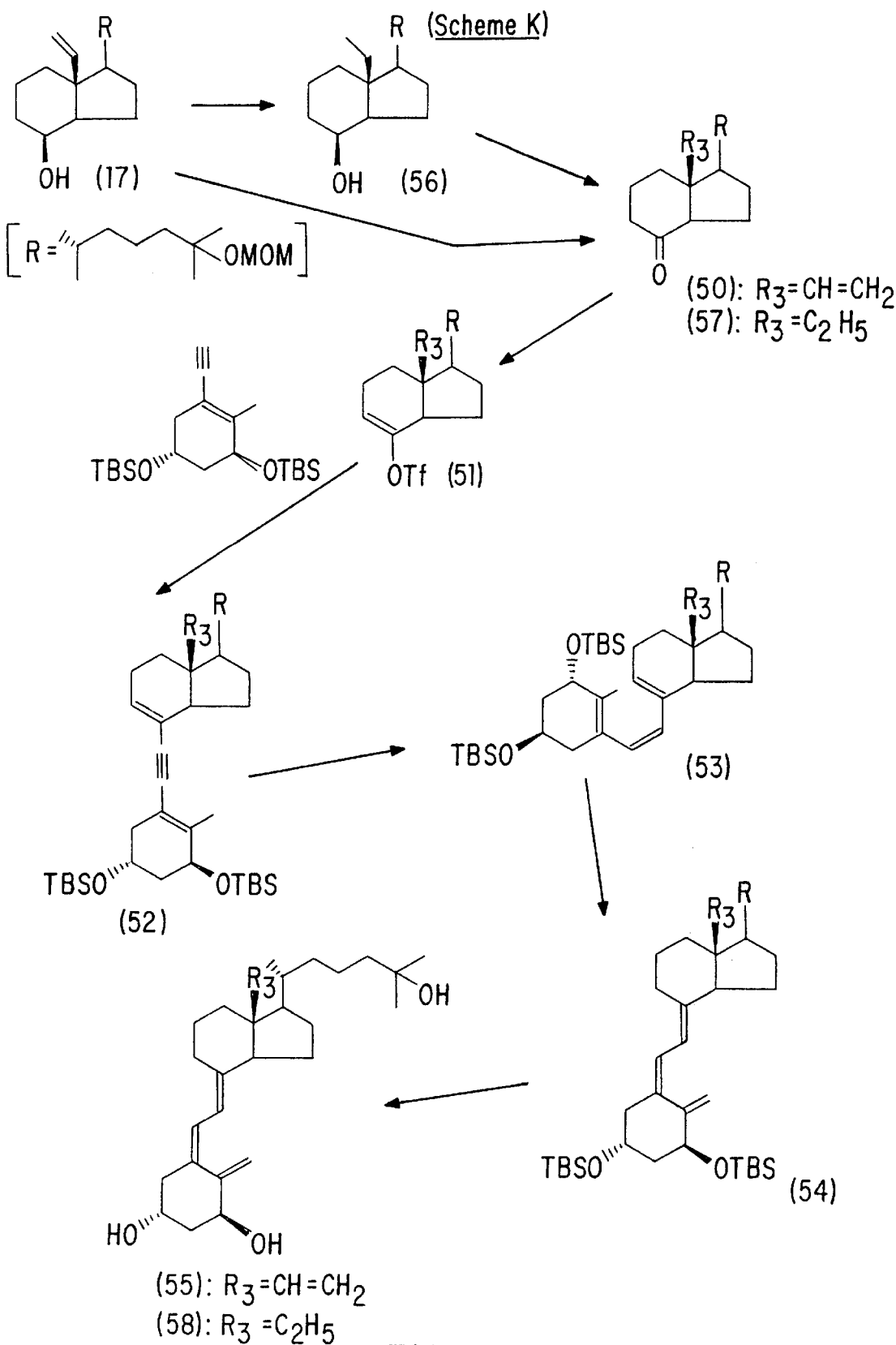
Figure 11:
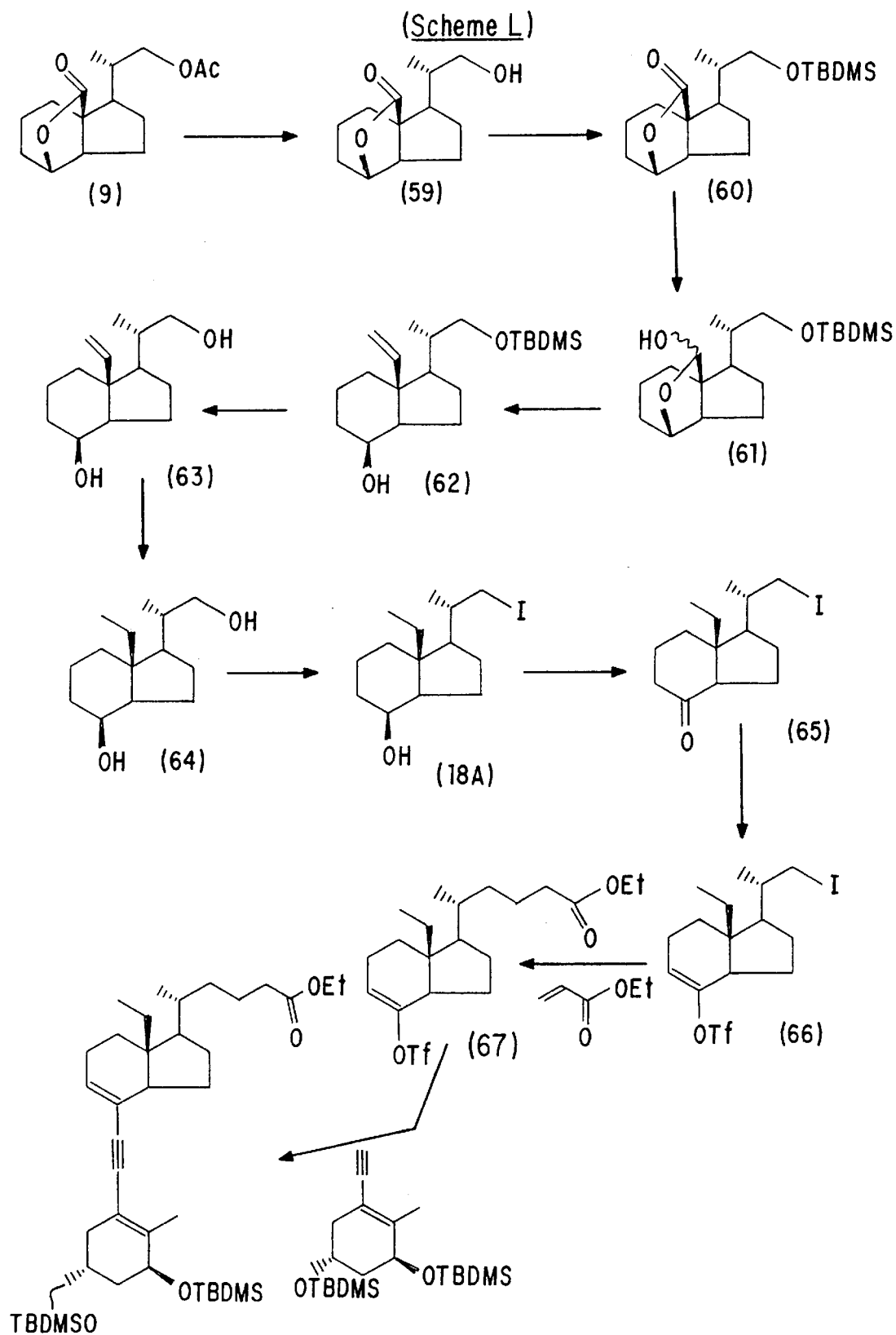
Figure 12A:
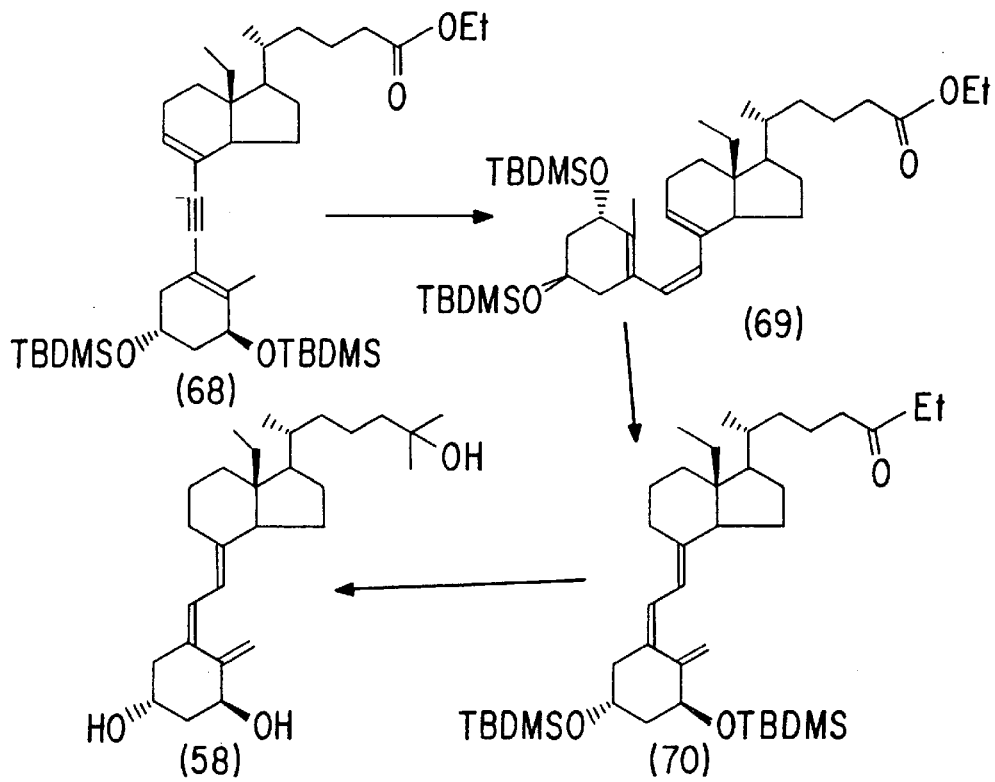
Figure 12B:
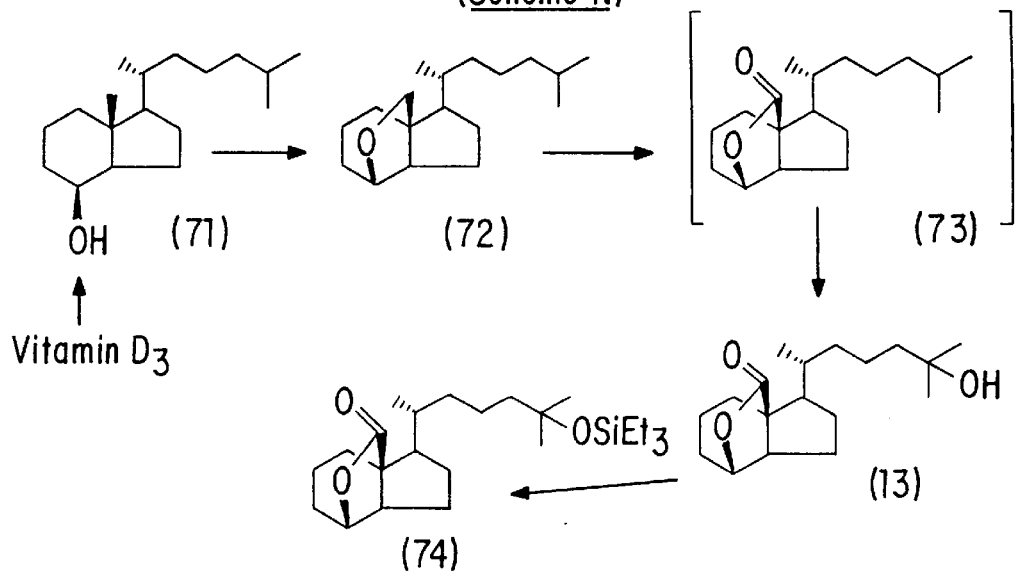

United States Patent [19]

Vallés et al.

[11] Patent Number: 6,072,062

[45] Date of Patent: Jun. 6, 2000

[54] SYNTHESIS OF $C_{18}$-MODIFIED VITAMIN D COMPOUNDS AND COMPOUNDS RESULTING THEREFROM

[75] Inventors: Maria J. Vallés; José L. Mascareñas; Antonio Mouriño, all of Santiago de Compostela, Spain; Sebastianus J. Halkes; Jan Zorgdrager, both of Weesp, Netherlands

[73] Assignee: Duphar International Research B.V., Weesp, Netherlands

[21] Appl. No.: 08/799,346

[22] Filed: Feb. 13, 1997

Related U.S. Application Data

[62] Division of application No. 08/333,305, Nov. 1, 1994, Pat. No. 5,637,742, which is a division of application No. 08/180,463, Jan. 12, 1994, Pat. No. 5,403,940, which is a continuation of application No. 07/907,121, Jul. 1, 1992, abandoned.

[30] Foreign Application Priority Data

Jul. 5, 1991 [EP] European Pat. Off. ............... 91201746
Jan. 20, 1992 [EP] European Pat. Off. ............... 92200154

[51] Int. Cl.$^7$ .................................................. C07C 401/00
[52] U.S. Cl. ........................................................... 552/653
[58] Field of Search ........................... 552/563; 558/428; 568/819

[56] References Cited

U.S. PATENT DOCUMENTS

| | | | |
|---|---|---|---|
| 4,508,651 | 4/1985 | Baggioline et al. | 522/654 |
| 4,612,308 | 9/1986 | Baggioline et al. | 552/653 |
| 4,613,594 | 9/1986 | Baggiolini et al. | 514/167 |
| 4,617,297 | 10/1986 | Boris et al. | 514/167 |
| 4,755,329 | 7/1988 | DeLuca et al. | 260/397.2 |
| 4,758,382 | 7/1988 | Steiling et al. | 55/653 |
| 5,237,110 | 8/1993 | DeLuca et al. | 568/665 |
| 5,246,925 | 9/1993 | DeLuca et al. | 514/167 |
| 5,617,297 | 10/1986 | Boris et al. | 514/167 |

FOREIGN PATENT DOCUMENTS

| | | |
|---|---|---|
| 0205025 | of 1986 | European Pat. Off. . |
| 0387077 | 9/1990 | European Pat. Off. . |
| 8607364 | of 0000 | WIPO . |

OTHER PUBLICATIONS

*Chemische Berichte*, vol. 91, No. 4, 1958, Weinheim De, pp. 781–791. H. Inhoffen et al., "Abbau der Vitamine D2 und D3 zum 8–Methyl–trans–hydrindanol–(4)–on–(1)".

*Journal of Chemical Research (S)*, No. 8, 1990, London, GB, pp. 240–241, R. Dorta et al., "Intramolecular Hydrogen Abstraction. (Diacetoxyiodo)–Benzene, a Useful Reagent for the Remote Functionalisation of Non–Activated Carbon Atoms".

*Mayo Clinic Proceesings*, vol. 56, No. 5, May 1981, Rochester, MN, US, pp. 327–333, R. Kumar et al., "Series on Pharmacology in Practice 11. Vitamin D in the therapy of Disorders of Calcium and Phosphorus Metabolism".

*Kidney International Supplement*, vol. 38, No. 29, 1990, New York, US pp. 22–27, A. Brown et al., "New Active Analogues of Vitamin D with Low Calcemic Activity".

*Proceedings of the Workshop on Vitamin D*, No. 7, 1988, Berlin, DE, pp. 925–934, M. Holick, "Vitamin D and the Skin: Site of Synthesis, Target Tissue and New Therapeutic Approach for Psoriasis".

*Proceedings of the Worshop on Vitamin D*, No. 7, 1988, Berlin, DE, pp. 1017–1020, E. Ritz et al., "Vitamin D Therapy in Renal Failure—Challenges and Problems for the Future".

*Tetrahedron Letters*, vol. 33, No. 11, Mar. 1992, Oxford, GB, pp. 1503–1506, M.J. Valled et al., "Functionalization of Vitamin D Metabolites at C–18 and Application to the Synthesis of 1–alpha, 18,25–Trihydroxyvitamin D3 and 18,25–Dihydroxyvitamin D".

J. Chm. Research Synop., 1990, pp. 240–241, R.L. Dorta et al, "Intramolecular Hydrogen Abstraction. (Diacetoxyiodo) Benzene, . . .".

Journal of the Chemical Society, Perkin Transactions 1, No. 3 Mar. 1989, pp. 405–411, P. De Armas et al, "Intramolecular . . .".

*Primary Examiner*—Jose' G. Dees
*Assistant Examiner*—Alton Pryor
*Attorney, Agent, or Firm*—Stevens, Davis, Miller & Mosher, L.L.P.

[57] ABSTRACT

The invention relates to a new vitamin D compound, substituted in the 18-position with an alkyl group, a hydroxy group, an alkoxy group, an alkenyl group, an alkynyl group, a fluorinated alkyl group or a fluorinated alkenyl group. The invention also relates to a method of preparing said vitamin D compound and to a lactone and a hydrindane intermediate. The vitamin D compound is of the general formula

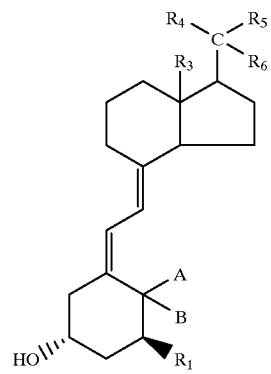

3 Claims, 12 Drawing Sheets

FIG. 9 (Scheme J)

SYNTHESIS OF C₁₈-MODIFIED VITAMIN D COMPOUNDS AND COMPOUNDS RESULTING THEREFROM

CROSS-REFERENCE TO RELATED APPLICATIONS

The present application is a division of U.S. application Ser. No. 08/333,305, filed Nov. 1, 1994, now U.S. Pat. No. 5,637,742; which, in turn, is a division of U.S. application Ser. No. 08/180,463, filed Jan. 12, 1994, now U.S. Pat. No. 5,403,940; which, in turn, is a continuation of U.S. application Ser. No. 07/907,121, filed Jul. 1, 1992, now abandoned.

The invention relates to a new vitamin D compound, to a method of preparing this compound and to an intermediate that can be used in this method.

It is generally known, that vitamin-D compounds or vitamin-D related compounds ("vitamin-D compounds") have a strong biological activity and may be used in all those cases in which problems with the calcium metabolism play a part. A few years ago it was found that various active vitamin-D compounds also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications.

It is therefore of the utmost importance to have the disposal of an arsenal of active vitamin-D compounds for said various application fields so as to be able to make the best possible choice of vitamin-D compounds for the application in view.

Vitamin-D compounds which are of interest for the applications mentioned hereinbefore are hydroxylated vitamin-D compounds, for example, 1α-hydroxyvitamin-D₃ or 1α-hydroxycholecalciferol, 24R-hydroxy-vitamin-D₃, 1α,25-dihydroxyvitamin-D₃, 25-hydroxyvitamin-D₃,24R,25-dihydroxyvitamin-D₃, 1α,24R-dihydroxyvitamin-D₃, 1α,24R,25-trihydroxyvitamin-D₃, 1α,25-dihydroxyvitamin-D₃-26,23-lactone, 25-hydroxyvitamin-D₃-26,23-lactone, 22-oxa-substituted vitamin-D compounds optionally having elongated $C_{17}$-side chains, vitamin-D₂ compounds hydroxylated in the 1α-, 24- and/or 25-position(s), and vitamin-D compounds having elongated $C_{17}$-side chains, such as 26-homo compounds, 26,27-dihomo compounds, 24,24-dihomo compounds and 24,24,24-trihomo compounds with or without double bonds and/or hydroxy groups in the side chains, as well as related vitamin-D compounds having a triple bond, e.g. a $C_{23}$–$C_{24}$-triple bond, or a $C_3$–$C_6$ cycloalkyl group, e.g. a $C_{24}$-cyclopropyl group, in the $C_{17}$-side chain. Furthermore, fluorinated and optionally hydroxylated vitamin-D compounds are of importance due to their biological activities.

From the above enumeration of vitamin D compounds it will be clear that the variations in the $C_{17}$-side chain of the vitamin D molecule are known to contribute to a certain selective activity, i.e. the intended activity without detrimental side-effects. In general, modified vitamin D compounds are potentially interesting substances, in principle suitable for the above-defined medical indications. In this connection there is a need for well accessible modified vitamin D compounds having a variety of $C_{17}$-side chains. As a matter of fact, both the starting compounds for the preparation of such vitamin-D compounds must be easily available or accessible, and the multistep preparation process must lead to the intended purpose with sufficient selectivity and efficiency. In addition, said purpose is not a specifically defined substance, but a variety of modified vitamin-D compounds, as indicated hereinbefore, from which a selection may be made at will. This means that the preparation process should be suitable without fundamental changes for the synthesis of an as large as possible number of different vitamin-D compounds.

It is therefore the objective of the present invention to provide a new class of vitamin D compounds, which is well accessible from readily available or accessible starting materials.

According to the present invention this objective can be achieved with a new vitamin D compound of the general formula

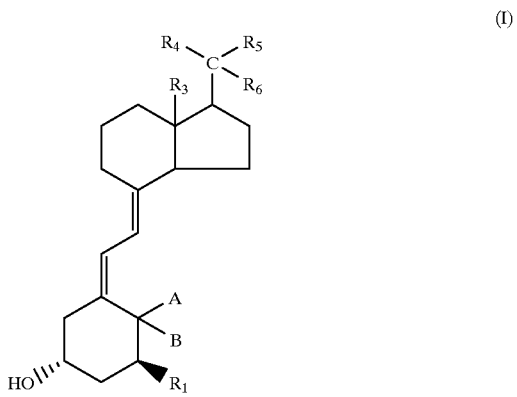

(I)

wherein $R_1$ is a hydrogen atom or a hydroxy group;

$R_3$ is a $C_2$–$C_5$ alkyl group, a hydroxy($C_1$–$C_4$)-alkyl group, a $C_1$–$C_4$ alkoxymethyl group, a $C_2$–$C_5$ alkenyl group, a $C_2$–$C_5$ alkynyl group, a fluorinated $C_2$–$C_5$ alkyl group or a fluorinated $C_2$–$C_5$ alkenyl group;

$R_4$ is a hydrogen atom or a $C_1$–$C_4$ alkyl group;

$R_5$ is a branched or non-branched, saturated or unsaturated aliphatic hydrocarbyl or hydrocarbyloxy group, which comprises 1 to 16 carbon atoms and which is optionally substituted with one or more substituents, selected from hydroxy groups, ether groups, oxo functions, cyclopropyl groups, lactone groups and fluorine atoms;

$R_6$ is a hydrogen atom or a $C_1$–$C_4$ alkyl group; and

A and B are each individually hydrogen atoms or methyl groups, or

A and B form together a methylene group.

Examples of suitable substituents $R_3$ are:

$C_2H_5$, $CH_2OH$, $CH=CF_2$, $CH_2CHF_2$, $CH=CH_2$ and $C\equiv CH$.

A hydroxy group in the vitamin D compound of the above formula I may be protected by a reaction with a suitable esterification or etherification agent. A suitable esterification agent is an alkylchlorocarbonate having 2 to 5 carbon atoms, or an aromatic carboxylic acid, a saturated aliphatic carboxylic acid having 1 to 4 carbon atoms, p-toluenesulphonic acid, methanesulphonic acid, trifluoroacetic acid or a derivative of these acids suitable for the esterification reaction. In order to protect hydroxy groups in the form of an ether, in principle any etherification agent known for this purpose is suitable: for example, a triphenylmethylhalide, 2,3-dihydropyrane, a trialkylsilylhalide, a diphenylalkylsilylhalide, an alkoxyalkylhalide, a trialkylsilylethoxymethylhalide, or a derivative thereof, the alkyl groups of which have 1 to 6 carbon atoms.

Particularly suitable for this purpose are trimethylsilylchloride, tert.-butyldimethylsilylchloride, dimethyl-(1,1,2-trimethylpropyl)silylchloride, trimethylsilyl-ethoxymethylchloride, methoxymethylchloride, methoxyethylchloride, tert.-butyldimethylsilyl trifluoroacetate, or trimethylsilylimidazole, because these etherification agents readily react with the hydroxy group to be protected to form an ether function, which on the one hand is sufficiently stable under the conditions of the reaction or reactions in view, but on the other hand can easily be removed [deprotection] to recover the original hydroxy group; tert.-butyldimethylsilylchloride is to be preferred, because the tert.-butyldimethylsilyl group has been found to be excellently suitable as a protective group.

The above new vitamin D compounds of the invention, presented by the general formula I, are valuable substances. The biological results, as illustrated in the Examples, indicate that these compounds are promising as biologically active substances and may be used in all above-mentioned pharmacotherapeutic indications, more in particular for the treatment of osteoporosis, renal osteodystrophy, osteomalacia, skin disorders such as psoriasis, eczema and dermatitis, myopathy, leukemia, breast and colon cancer, osteosarcomas, cutaneous squamous cell carcinomas, certain immunological disorders, and transplant rejections. Furthermore, the new vitamin D compounds of the invention may be used for wound healing and may be incorporated in cosmetic compositions, such as creams, lotions, ointments and the like, in order to preserve, condition and/or protect the skin and to improve various skin conditions, such as wrinkles, dry skin, skin slackness and insufficient sebum secretion.

A vitamin D compound is preferred, having the above general formula I,
wherein $R_1$, $R_3$, A and B have the above meanings, $R_4$ is a methyl group, and R is a hydrogen atom or a methyl group, and $R_5$ is an aliphatic hydrocarbyl group selected from the group consisting of 3,4-dimethylpenten-1-yl, 3,4-dimethyl-4-hydroxypenten-1-yl, 3-hydroxy-4-methylpentyl, 4-hydroxy-4-methylpentyl,3,4-dihydroxy-4-methylpentyl,3,3-difluoro-4-hydroxy-4-methylpentyl, 3-methylbutoxy, 3-hydroxy-3-methylbutoxy, 3-cyclopropyl-3-hydroxypropen-1-yl and 3-cyclopropyl-3-hydroxy-3-methylpropen-1-yl; or its corresponding 24-homo-, 26-homo-, 24,24-dihomo-, 26,27-dihomo-, 24,26,27-trihomo- or 24,24,26,27-tetrahomo-vitamin D analogue.

It is a special merit of the present invention that the above new vitamin D compound of the invention can easily be prepared from readily available starting materials. In particular, it has been found, that the modification at $C_{18}$ can easily be achieved by using a suitable methyl-substituted compound, e.g. a 7a-methylhydrindan-4-ol compound, as the starting material. Consequently, the present invention also relates to a method of preparing the vitamin D compound as defined above, which method is characterized in that a hydrindane compound of the general formula

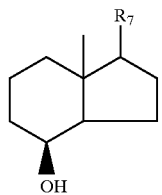

(II)

wherein $R_7$ is a branched or non-branched, saturated or unsaturated aliphatic hydrocarbyl group, which comprises 1 to 16 carbon atoms and which is optionally substituted with one or more substituents selected from protected hydroxy groups, ether groups, protected oxo functions, $C_1$–$C_4$ alkyl ester groups, cyclopropyl groups, and fluorine atoms;

is oxidized to a lactone intermediate of the general formula (III)

wherein $R_7$ has the above meaning, after which said lactone intermediate is reduced and then subjected, if desired, to a reaction sequence to introduce substituent $R_3$ and to convert substituent $R_7$ in a manner known per se for related compounds into substituent $R_4C(R_5) R_6$;

after which the hydrindane compound obtained, having the general formula (IV)

is oxidized to the corresponding hydrindane-4-one compound and is then reacted, in a manner known per se for related compounds, either (a) with a Wittig reagent of the general formula (V)

wherein $R_1'$ is a hydrogen atom or a protected hydroxy group, $R_2$ is a protected hydroxy group, and A and B have the above meanings, or (b), after enolization, with an enyne compound of the general formula

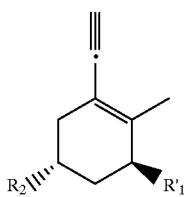

(VI)

wherein R₁' and R₂ have the above meanings, followed by hydrogenation and equilibration; the product obtained, if desired, being deprotected.

It is an additional merit of the present invention, that the starting hydrindane compound of the above formula II can easily and simply be prepared from a readily available seco steroid as a starting material, and that therefore certain vitamin D compounds are better accessible by using this compound as a synthon. Said hydrindane compound can be prepared in a simple manner by subjecting a seco steroid of the general formula

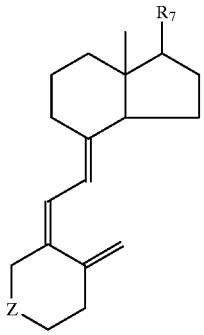

(XIII)

wherein

R₇ has the above meaning, and

Z is a hydroxymethylene group, a carbonyl group or a ketalised carbonyl group, or a hydroxy-protected derivative thereof as defined above, to an oxidative cleavage of the $C_7$–$C_8$ double bond, after which the hydrindan-4-one product obtained is converted with a suitable reductant, a compound of the above general formula II being formed.

The above oxidative cleavage can be performed by ozonolysis in a conventional manner, viz. by addition of ozone, followed by a reductive cleavage of the formed ozonide. Alternatively, said oxidative cleavage can be carried out by an oxidation reaction with the aid of a suitable oxidant, preferably with potassium permanganate, followed by a treatment with lead tetraacetate and by reduction.

Particularly suitable as a starting material for the above preparation method is a seco steroid of the above general formula XIII, wherein both R₇ and Z are ketalized acetyl and carbonyl groups, respectively, because such a compound can simply be prepared by irradiating the readily available 9,10-secopregna-5,7,10(19)-triene-3,20-diketal.

Equally suitable as starting materials are vitamin D₂ compounds, i.e. a compound of the above general formula XIII, wherein Z is a hydroxymethylene group and R₇ is a 1,4,5-trimethylhexen-2-yl group. Examples are presented in Scheme A.

It will be self-evident, that Scheme A, as well as the other Schemes attached, only serves to illustrate the invention.

Various modifications and variations are feasible within the framework of the present invention.

In the attached Schemes the following abbreviations are used:

TBS=t.butyldimethylsilyl;
LDA=lithium diisopropyl amide;
Me=methyl;
X=halogen;
φ=phenyl;
mCPBA=m-chloroperbenzoic acid;
sBu=sec.butyl;
Ts=toluenesulphonyl (tosyl);
Ac=acetyl;
TMS=trimethylsilyl;
Et=ethyl;
Pr=n-propyl;
Tf=trifluoromethylsulphonyl;
tBu=tert.butyl;
Py=pyridine;
DIBAL-H=diisobutylaluminium hydride; and
THF=tetrahydrofuran.

Reaction conditions Scheme A; (1)→a(2) and (3)→(4):

Addition of ozone at decreased temp. in dichloromethane, methanol, ethanol, etc., in presence of pyridine, followed by reduction of ozonide by LiAlH₄, NaBH₄, DIBAL-H or other complex metal hydrides.

Alternative I: oxidation by KMnO₄ in H₂O/EtOH at decreased temp., oxidative cleavage by Pb(OAc)₄ and reduction.

Alternative II: epoxidation by mCPBA in dichloromethane at decreased temp., followed by oxidative cleavage.

Hydrindane compounds obtainable from the particularly suitable seco steroid, as defined above, are new. Therefore the present invention also relates to a hydrindane compound of the general formula

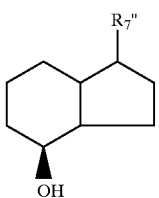

(IIa)

wherein

R₇" is a ketalized acetyl group, preferably a 1,1-dimethoxyethyl group, a 1,1-diethoxyethyl group or a 2-methyl-1,3-dioxacyclopent-2-yl group.

The resulting hydrindane compound of the general formula II is a suitable starting substance for the synthesis of new vitamin D compounds in that this substance easily allows modification of the $C_{7a}$-methyl group through the lactone intermediate of the general formula III as defined above. Said lactone intermediate can easily be produced from the above hydrindane compound by an oxidation reaction, preferably in two separate oxidation steps. In the first oxidation step an oxidant is used which is preferably selected from lead tetraacetate and phenyl iodosodiacetate, and subsequently with silver acetate, to obtain the tetrahydrofuran intermediate, having the general formula

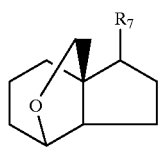

(XIV)

wherein $R_7$ has the above meaning. In the second oxidation step an oxidant is used which is preferably selected from ruthenium oxide, chromium trioxide, benzyl triethylammonium permanganate and trichloroisocyanuric acid, to obtain the lactone intermediate of the general formula III above. Examples are also presented in Scheme A.

As a particular aspect of the present invention it has been found, that by using ruthenium oxide as the oxidant in said second oxidation step, a terminal isopropyl group in the hydrindane molecule can be oxidized to the corresponding 2-hydroxyprop-2-yl group, simultaneously with the lactone formation. In this manner, for instance 25-hydroxyvitamin D compounds can be synthetized very easily. Reaction conditions Scheme A; (2)→(6),(4)→(9) and (4)→(13):

reaction (2)→(5): Pb(OAc)$_4$ in benzene at reflex temp.

reaction (5)→(6): oxidation with RuO$_2$ in presence of NaIO$_4$ in mixture of CH$_3$CN/H$_2$O/CCl$_4$ at room temp.

reaction (4)→(7): acetylation with Ac$_2$O in Py at approx. 0° C. reaction (7)→(8): see (2)→(5).

reaction (8)→(9): see (5)→(6). reaction (4)→(10): iodination with I$_2$/P(Ph)$_3$ in presence of imidazole in THF at approx. 0° C.

reaction (10)→(11): reaction with methylacrylate in presence of Zn/ICu under sonication in EtOH/H$_2$O.

reaction (11)→(12): see (2)→(5).

reaction (12)→(13): reaction with MeLi in THF at approx. 0° C., followed by oxidation as in (5)→(6).

It will be clear from Scheme A, that the $C_{18}$-modification of the vitamin D molecule can be performed at different stages of the $C_{17}$-side chain build-up procedure.

The lactone intermediate of the general formula III is new. Therefore the present invention also relates to said lactone intermediate, which can be prepared as described above.

Said lactone intermediate is to be considered as a versatile intermediate, permitting interesting modifications of the molecule and finally resulting in $C_{18}$-modified vitamin D compounds. To obtain a hydroxymethyl group at $C_{13}$ of the final vitamin D molecule, said lactone intermediate can first be reduced with a suitable reducing agent, e.g. with LiAlH$_4$. This reaction is presented in Scheme B, wherein $R_{10}$ encompasses the substituents shown in compounds (6) and (13) of Scheme A. The hydroxymethyl group can be converted, if desired, to the corresponding $C_{1-4}$ alkylether by any conventional etherification reaction. With a different reducing agent, preferably DIBAL-H, the reduction reaction results in a reduction of the lactone function to the lactol function, which intermediate is suitable for reacting with a Wittig reagent: Scheme B. The product obtained by the last reaction can be converted, if desired, as indicated in Scheme B.

Reaction conditions Scheme B: (14)→(15) and (14)→(16) etc.:

reaction (14)→(15): LiAlH$_4$ in THF at approx. 0° C.

reaction (14)→(16): DIBAL-H in toluene at decreased temp. reaction (16)→(17): φPCH$_3$Br in THF in presence of tBuOK at room temp.

reactions (16)→(21) and (16)→(19): corresp.

reactions (17)→(18) and (21)→(22): catalytic hydrogenation in suitable solvent.

reaction (19)→(20): under influence of BuLi in THF at decreased temp.

The product thus obtained is a suitable synthon for the preparation of $C_{18}$-modified vitamin D compounds having a variety of $C_{17}$-side chains.

In an equally attractive manner the new vitamin D compounds of the present invention can be prepared starting from a hydrindane compound of the general formula

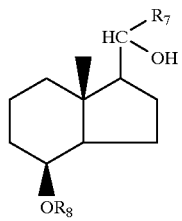

(VII)

wherein $R_7$ has the above meaning, and $R_8$ is a hydroxy-protecting group, as defined above.

It has been found that said hydrindane compound can easily be oxidized to a lactone intermediate of the general formula

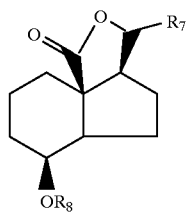

(VIII)

wherein the symbols have the above meanings.

This lactone intermediate is also a versatile intermediate for the synthesis of various vitamin D compounds and is completely comparable with the lactone intermediate of formula III, described above. Modification of the 7a-methyl group of the hydrindane structure, as described for lactone intermediate III, can be performed in the same manner starting from the above intermediate VIII, ultimately producing the desired $C_{18}$-modified vitamin D compound. Both the synthesis of lactone intermediate VIII and the conversion of this intermediate into $C_{18}$-modified vitamin D compound proceed under the same conditions as described above for lactone intermediate III.

It will be understood, that the invention also relates to the lactone intermediate of the general formula VIII per se.

Alternatively, for the synthesis of $C_{18}$-modified vitamin D compounds, a hydrindane compound of the general formula

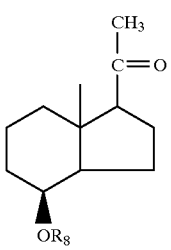

(X)

wherein $R_6$ has the above meaning, can be used as a starting material. This compound is first converted to the corresponding cyano-hydrin of the general formula

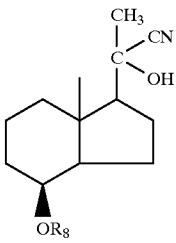

(XI)

after which this intermediate is converted to a hydrindane intermediate of the general formula

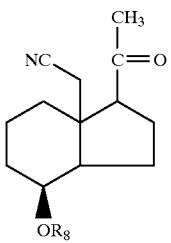

(XII)

by $Pb(OAc)_4$ in the presence of $I_2$ and under the influence of heat and light. The cyano group can then be converted in a manner known per se to produce substituent $R_3$ in the 7a-position of the hydrindane structure. Build-up of the desired $C_{17}$-side chain of the vitamin D molecule and introduction of the A-ring system can be performed as described below.

The desired $C_{17}$-side chain can be built up in a manner known per se for related compounds, e.g. as described by Baggiolini et al. in J.Am.Chem.Soc. 104, 1982, 2945–2948, and by Wicha et al. in J.C.S.Perkin I, 1978, 1282–1288, and in J.C.S.Chem. Comm., 1975, 968–969. After said side chain formation, in which group $R_4C(R_5)R6$ is substituted for $R_7$, a hydrindane compound is obtained, having the general formula

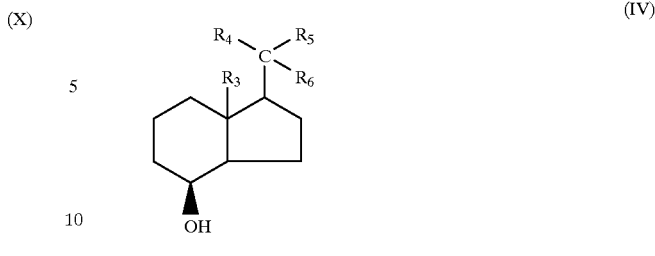

(IV)

wherein the symbols have the meanings defined above.

After said $C_{17}$-side chain formation, the A-ring system of the vitamin-D compound can be introduced by first converting the hydroxy group to a keto group via oxidation, and by then converting the keto compound thus obtained with a Wittig reagent of the general formula

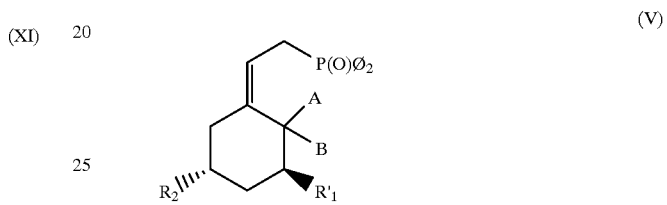

(V)

wherein
 $R_1'$ is a hydrogen atom or a protected hydroxy group,
 $R_2$ is a protected hydroxy group, and
A and B have the above meanings, the product obtained, if desired, being deprotected. This A-ring introduction is described in an article by Wovkulich et al.: Tetrahedron 40, 1984, 2283–2296.

Alternatively, the A-ring can be introduced by converting said keto compound, after enolization, with an enyne compound of the general formula

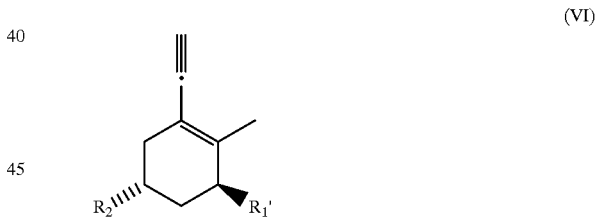

(VI)

wherein the symbols have the above meanings, followed by hydrogenation and equilibration.

The product obtained can equally be deprotected. This latter A-ring introduction, visualized in Scheme E, is described by Lythgoe et al in J.Chem.Soc.(C), 1971, 2960–2966, and in J. C. S. Perkin I, 1974, 2654–2657, and by Mourino et al. in Tetrahedron Letters 29, 1988, 1203–1206.

After the above reactions have been performed, the synthesis of the desired vitamin-D compound has been completed.

In Scheme C an example of the preparation of vitamin D compounds according to the above synthetic pathway is presented. Substituent $R_3$ is defined above, as well as A and B. A and B preferably form together a methylene group or both represent hydrogen atoms.

Reaction conditions Scheme C

Reaction (23)→(24): alkaline saponification in an alcohol; followed by iodination with $I_2$ in presence of $PPh_3$ and imidazole, in THF as solvent.

Reaction (24)→(25): reaction with methacrylate under sonication in presence of Zn and CuI.

Reaction (25)→(26): reaction with MeMgBr in THF at approx. 0° C.

Reaction (26)→(27) proceeds in two reaction steps: oxidation, e.g. with a Cr-containing oxidant; and reaction with trimethylsilylimidazole to protect free OH.

Reaction (27)→(28) proceeds via a Wittig reaction under conventional Wittig conditions and a deprotection (see above).

The desired $C_{17}$-side chain can also be built up in a different manner known per se for related compounds, e.g. as described by Kyler et al. in J.Am.Chem.Soc. 105, 1983, 619–621, and in J.Org.Chem. 49, 1984, 1084–1090, by Narwid et al. in Helv.Chim.Acta 57, (Fasc. 3), 1974, 771–781. After the $Cu_7$-side chain formation, the A-ring system of the vitamin-D compound can be introduced as described above.

Scheme D illustrates the above synthetic reactions.

Reaction conditions Scheme D

Reaction (29)→(30) proceeds via the following reaction steps: Metalation of the substituted propene using sBuLi (10% HMPA-THF; decreased temp.) and condensation with compound (29); conversion with sBuLi (10% HMPA-THF, decreased temp.) and reaction with pentanone-3; reaction with $NiCl_2$ in aqueous tBuOH; Raney nickel reduction finally leads to compound (30).

Reaction (29)→(31) proceeds via the following reaction steps: Grignard reaction with vinylmagnesiumchloride in THF; reaction with diketene in decaline in the presence of s-collidine; cat. hydrogenation ($H_2$/PtO); and finally Grignard reaction with methylmagnesiumbromide in diethylether.

Reaction (30,31)→(32,38): see Reaction Scheme C.

In another, equally interesting chain-extending reaction, the carbonyl group of the starting hydrindane compound is first reduced, e.g. with sodium borohydride, or is first converted in a Grignard reaction with a methylmagnesium halogenide, to the corresponding hydroxy compound. O-alkylation of this hydroxy compound, followed by the above-described introduction of the A-ring system, results in 22-oxa-substituted vitamin-D compounds. The above O-alkylation can be performed in a manner known per se for related compounds, e.g. as described in the recently published international patent applications Wo 90/09991 and WO 90/09992.

Scheme E is an illustration of the above synthetic reactions.

Reaction conditions Scheme E

Reaction (29)→(33): Reduction with $LiAlH_4$ or $NaBH_4$.

Reaction (29)→(34): Grignard reaction with MeMgI under conventional Grignard conditions.

Reaction (33,34)→(35,36) proceeds via the following reaction steps: Deprotonation with NaH in THF, followed by reaction with ω-bromoalkylether; desilylation with tetrabutylammonium fluoride in THF, followed by oxidation with a Cr-containing oxidant; Wittig reaction under conventional Wittig conditions, followed by deprotection.

Reaction (33,34)→(35,36) proceeds alternatively via the following reaction steps: Deprotonation followed by reaction with ω-bromoalkylether (see above); desilylation followed by oxidation (see above); reaction with LDA, followed by reaction with phenyl trifluoromethylsulfonimide; reaction with enyne under influence of a Pd-cat. and $Et_3N$ in DMF (increased temp.); finally catalytical hydrogenation ($H_2$/Pd-$BaSO_4$), heating and deprotection (see above). The vitamin-D compounds prepared as described above can occur in different diastereoisomeric configurations. The present invention includes the preparation of such diastereoisomers in pure form and of mixtures of such stereoisomers. In addition, product (35), as prepared above according to Scheme E, can occur in two different stereochemical configurations at C-20, viz. the R- and the S-configuration.

The invention will now be described in greater detail with respect to the following specific examples.

A survey of the reaction equations, illustrated in the Examples, is shown in the Reaction Schemes attached, in particular in Schemes F and following. The compound numbers correspond, if possible, to the numbers used in Schemes A and B. The reaction steps described in the Examples are indicated with the numbers of starting compound and product, corresponding with those used in the Schemes. In the spectral data the numbering corresponds to the well-known numbering of the C-atoms in the vitamin D molecule.

EXAMPLE I

Reaction (3)→(4):

Vitamin $D_2$ (8.00 g, compound 3) is dissolved in 700 ml methanol and 7 ml pyridine. After flushing with $N_2$ for 30 minutes, ozone is passed through the solution, cooled to −80° C., during 2.5 hours. The resulting ozonide is directly reduced by adding 2 g $NaBH_4$ to the reaction mixture, followed by stirring for 20 minutes at −80° C. Addition of another portion of $NaBH_4$ (1 g), after 30 min. at room temperature and again another 1 g portion of $NaBH_4$ after standing overnight at room temperature. The reaction mixture is concentrated and continuously extracted with diethylether for 24 hours. The organic layer is dried, filtered, and evaporated to dryness. The residue is chromatographed over silicagel (eluent 25% EtOAc/petroleum ether), yielding 5.71 g of product (4). Rf (30% EtOAc/petroleum ether) 0.10; m.p. 110° C.

$^1$H-NMR ($CDCl_3$, δ): 0.94 (s, 3H, $CH_3$-18), 1.01 (d, J=6.6 Hz, 3H, $CH_3$-21), 3.37 (dd, J=10.5, 6.7 Hz, 1H, H-22), 3.62 (dd, J=10.5, 3.5 Hz, 1H, H-22), 4.07 (9, 1H, H-8).

EXAMPLE II

Reaction (4)→(10)

A solution of 1.056 g of compound (4), 1.430 g $PPh_3$ and 1.016 g imidazole in 25 ml dry THF under argon is cooled in an ice-water bath. Iodine (1.391 g) is added and the temperature is maintained at approx. 0° C. for 15 min. After allowing the reaction mixture to reach room temperature, THF is evaporated, satd. $NaHCO_3$ is added and the reaction mixture is extracted twice with diethylether. The organic phase is separated, washed with 5% $Na_2SO_3$ solution, dried, filtered, concentrated under reduced pressure and finally filtered over silica gel (eluent: 25% EtOAc/hexane). The desired product is obtained as a viscous liquid in a yield of 1.533 g.

$^1$H-NMR ($CDCl_3$, δ):0.98(s, 3H, $CH_3$-18), 1.01 (d, J=5.40 Hz, 3H, $CH_3$-21), 3.19 (dd, J=4.60, 9.61 Hz, 1H, CHHI), 3.27 (dd, J=7.39, 9.54 Hz, 1H, CHHI), 4.10 (a, 1H, H-8).

$^{13}$C-NMR ($CDCl_3$, δ): 14.28, 17.28, 20.57, 21.07, 22.30, 26.45, 33.50, 36.30, 40.05, 41.78, 52.28, 55.87, 69.15.

EM [70 eV, m/z (%)]: 322 ($M^+$, 0.3), 307 (16.5), 177 (99.6), 135 (50.7), 111 (100).

EXAMPLE III

Reaction (10)→(11)

Zn (1.785 g) and 2.229 g purified CuI are introduced under argon into 3 ml oxygen-free EtOH/H$_2$O. This reaction mixture is sonicated under argon for 10 min. To this mixture is added dropwise a solution of 1.264 g of compound (10) in 6 ml (66.7 mmoles) freshly distilled methylacrylate at room temperature under argon and while sonicating. Sonication is continued for 30 minutes. After addition of 10 ml NH$_4$Cl, the reaction mixture is again sonicated for 10 minutes. Filtration over celite, washing with diethylether, washing of the diethylether phase with saturated NaCl solution and drying produces a solution in ether, which, after evaporation to dryness, yields a residue. This residue is purified by column chromatography (silica; eluent: 5–20% EtOAc/hexane), affording the desired product (11) in a yield of 615 mg.

EXAMPLE IV

Reaction (11)→(12):

Under protection against light, 7.210 g of Pb(OAc)$_4$ is added to a cooled, stirred solution of compound (11) (1.994 g) in 275 ml dry benzene under argon. After 20 hours reflux a second portion of 940 mg of Pb(OAc)$_4$ is added, and the reaction mixture is refluxed for another 10 hours. After addition of saturated NaCl solution, the mixture is extracted with EtOAc and the organic phase is dried, filtered and concentrated under reduced pressure. The residue is purified by column chromatography (eluent: 5%–20% EtOAc/hexane), yielding 1.22 g of the desired product (12). $^1$H-NMR (CDCl$_3$,δ): 0.90 (d, J=6.71 Hz, 3H, CH$_3$-21), 3.66 (s, 3H, COOCH$_3$), 3.68 (d, J=8.14 Hz, 1 H, CHHO), 3.74 (d, J=8.20 Hz, 1H, CHhO), 4.13 (d, J=4.33 Hz, 1H, H-8). $^{13}$C-NMR (CDCl$_3$,δ): 19.04, 19.04, 21.76, 25.11, 29.18, 32.56, 34.23, 35.64, 37.49, 37.49, 51.30, 51.72, 54.28, 58.14, 70.93, 79.03, 174.12.

EXAMPLE V

Reaction (37)→(11):

NaBH$_4$ (1.088 g) is added in small portions to a cooled (0° C.) and stirred solution of 2.014 g of compound (37) in 25 ml of dry methanol. After 30 minutes the solvent is evaporated. The residue is dissolved in diethylether, washed with water, dried and filtered. Column chromatography (eluent: 10% EtOAc/hexane) yields 1.663 g of product (11), identical with the product of Example III.

EXAMPLE VI

Reaction (12)→(12A):

MeLi (17.985 moles) is added to a solution of 2.289 g (8.175 mmoles) of compound (12) in 125 ml dry diethylether, cooled at –80° C., under argon while stirring. At room temperature 5 ml water is added and the reaction mixture is extracted with diethylether, washed with satd. NaCl solution, dried and filtered. Flash column chromatography (eluent: 10–25% EtOAc/hexane) yields 2.050 g of product (12A).
$^1$H-NMR (CDCl$_3$, δ): 0.89 (d, J=6.60 Hz, 3H, CH$_3$-21), 1.20 (s, 6H, CH$_3$-26,27), 3.70 (d, J=8.18 Hz, 1H, CHHO), 3.72 (d, J=8.22 Hz, 1H, CHHO), 4.13 (d, J=4.33 Hz, 1H, H-8).
$^{13}$C-NMR (CDCl$_3$,): 19,08, 19.18, 21.12, 25.17, 29.14, 29.26, 29.30, 32.61, 36.76, 37.55, 37.78, 44.22, 52.02, 54.34, 58.20, 70.95, 71.03, 79.09.

EXAMPLE VII

Reaction (12A)→(13):

NaIO$_4$ is added to a solution of 267 mg of compound (12A) in a mixture of CCl$_4$/H$_2$O/CH$_3$CN (4:8:4 ml). After vigorous stirring for one minute RuO$_2$.H$_2$O is added. After vigorous stirring for 17 days, 25 ml water is added and the reaction mixture is extracted with CH$_2$Cl$_2$ (3×25 ml). Drying of the organic phase, filtration and concentration yields a residue, which is purified over a silica gel column (eluent: 5%–15% EtOAc/hexane). The desired product (13) is obtained in a yield of 157 mg. $^1$H-NMR (CDCl$_3$,δ): 1.10 (d, J=6.53 Hz, 3H, CH$_3$-21), 1.21 (s, 6H, CH$_{13}$-26,27), 4.56 (d, J=4.55 Hz, 1H, H-8).

EXAMPLE VIII

Reaction (13)→(14):

Chloromethoxymethane (0.160 ml, 2.163 mmoles), diisopropyl-ethylamine (0.378 ml, 2.163 mmoles) and 4-dimethylaminopyridine (17 mg, 0.139 mmoles) are added to a stirred, cooled (0° C.) solution of 145 mg of compound (13) in 8 ml dry CH$_2$Cl$_2$ under argon. After stirring for 18 hours, water (10 ml) is added and the reaction mixture is extracted with CH$_2$Cl$_2$. The organic phase is washed with 10% hydrochloric acid and with saturated NaCl solution. After filtration through a silica gel column (eluent: 15% EtOAc/hexane), 163 mg of the desired product (14) is obtained.
$^1$H-NMR (CDCl$_3$, δ): 1.10 (d, J=6.32 Hz, 3H, CH$_3$-21), 1.21 (s, 6H, CH$_3$-26,27), 3.37 (s, 3H, OCH$_3$), 4.56 (d, J=3.73 Hz, 1H, H-8), 4.71 (5, 2H, OCH$_2$O)

EXAMPLE IX

Reaction (14)→(16):

A 1M solution of DIBAL-H in hexane (0.541 mmoles) is added dropwise to a cooled (–80° C.) and stirred solution of 135 mg of compound (14) in 2.5 ml of dry toluene under argon. After stirring for 2 hours, a solution of isopropanol in toluene is added. The reaction mixture is allowed to reach room temperature, after which water is added and the emulsion is filtered over celite. The organic phase is washed with saturated NaCl solution, dried, filtered, concentrated under reduced pressure and chromatographed over silica gel (eluent: 15–25% EtOAc/hexane, yielding 101 mg of the desired product (16).

EXAMPLE X

Reaction (16)→(17):

In an argon atmosphere tBuOK (124 mg) and 395 mg MeP$^+$Ph$_3$Br- are dissolved in 5 ml dry THF. After reflux for 20 hours, 2.765 ml of this solution is added via a syringe to a stirred solution of compound (16) (75 mg) in 4 ml dry THF, equally under argon. Reflux for 12 hours, evaporation of the THF, dissolution in 10 ml EtOAc and extraction (twice) with water. The organic phase is washed with saturated NaCl solution, dried, filtered and concentrated. The residue is purified by column chromatography over silica gel (eluent: 15% EtOAc/hexane), yielding 60 mg of the desired product (17).
$^1$H-NMR (CDCl$_3$,δ): 0.83 (d, J=6.7 Hz, 3H, CH$_3$-21), 1.21 (s, 6H, CH$_3$-26,27), 3.37 (8, 3H, OCH$_3$), 3.95 (s, 1H, H-8), 4.71 (s, 2H, OCH$_2$O), 5.27 (m, 2H, CH$_2$=), 6.00 (dd, J=9.6, 18.6 Hz, 1H, CH=).
$^{13}$C-NMR (CDCl$_3$,δ): 17.04, 17.75, 20.38, 22.26, 26.25, 26.34, 27.13, 33.65, 35.26, 35.83, 36.06, 42.24, 48.39, 54.83, 55.04, 57.09, 69.91, 76.32, 91.01, 114.43, 138.20.

EXAMPLE XI

Reaction (4)→(7):

Freshly distilled $Ac_2O$ is added dropwise to a cooled (0° C.) stirred solution of compound (4) (1.435 g) in 9 ml of dry pyridine under argon. After 12 hours at approx. 0° C., ice and $NaHCO_3$ are added and the reaction mixture is extracted with diethylether. The organic phase is washed with 10% hydrochloric acid, saturated $NaHCO_3$ solution, $CuSO_4$ solution, saturated NaCl solution, dried, filtered and concentrated. The residue is crystallized from diethylether/hexane, yielding 1.495 g of the desired product (7).

$^1$H-NMR ($CDCl_3$,δ): 0.96 (s, 3H, $CH_3$-18), 1.00 (d, J=6.61 Hz, 3H, $CH_3$-21), 2.05 (s, 3H, $CH_3COO$), 3.78 (dd, J=7.44, 10.68 Hz, 1H, H-22), 4.10 (dd, J=3.44, 9.8 Hz, 1H, H-22), 4.10 (s, 1H, H-8). $^{13}$($CDCl_3$, δ): 13.51, 16.97, 17.36, 20.92, 22.55, 26.60, 33.60, 35.34, 40.24, 41.97, 52.36, 53.33, 69.20, 69.44.

EXAMPLE XII

Reaction (7)→(8):

In a corresponding manner as described in Example IV the above reaction is performed, producing the desired product (8) in a yield of 67%. Rf (25% EtOAc/hexane) 0.6.

$^1$H-NMR ($CDCl_3$, δ): 0.99 (d, J=6.48 Hz, 3H, $CH_3$-21), 2.05 (s, 3H, $CH_3$acetate), 3.68 (d, J=8.18 Hz, 1H, CHHO), 3.74 (d, J=8.19 Hz, 1H, CHHOAc), 3.81 (dd, J=7.4, 10.84 Hz, 1H, CHHOAc), 4.16 (d, J=4.25 Hz, 1H, H-8).

EM (70 eV, m/z(%)]: 252 ($M^+$, 5.9), 192 (28.6), 177 (24.0), 149 (28.0), 124 (36.9), 111 (100), 96 (35.9), 81 (57.0).

EXAMPLE XIII

Reaction (8)→(9,14A):

In a corresponding manner as described in Example VII the above reaction is performed, producing the desired product in a yield of 76%. $^1$H-NMR ($CDCl_3$,δ): 1.18 (d, J=6.66 Hz, 3H, $CH_3$-21), 2.05 (s, 3H, $CH_3COO$), 3.89 (dd, J=6.28, 10.84 Hz, 1H, CHHOAC), 4.06 (dd, J=3.51, 10.84 Hz, 1H, CHHOAC), 4.58 (d, J=4.7 Hz, 1H, H-8). EM [70 eV, m/z(%)]: 266 ($M^+$, 0.1), 223 (20.6), 206 (87.8), 161 (62.4), 147 (95.4), 121 (100), 105 (30.6), 91 (52.8), 79 (67.3).

EXAMPLE XIV

Reaction (9,14A)→(16A):

In a corresponding manner as described in Example IX the above reaction is performed, producing the desired product (16A) in a yield of 84%. Rf (60% EtOAc/hexane) 0.3.

EXAMPLE XV

Reaction (16A)→(17A):

In a corresponding manner as described in Example X the above reaction is performed, resulting in the desired product (17A). $^1$H-NMR ($CDCl_3$,δ): 0.95 (d, J=6.11 Hz, 3H, $CH_3$-21), 3.40 (dd, J=5.72, 10,47 Hz, 1H, CHHOH), 3.59 (dd, J=2.62, 10.56 Hz, 1H, CHHOH), 3.96 (s, 1H, H-8), 5.29 (m, 2H, CH=), 6.00 (dd, J=10.76, 16.82 Hz, 1H, CH=).

EXAMPLE XVI

Reaction (17A)→(18A):

Compound (17A) is hydrogenated at room temperature in methanol under the influence of Pd-C. Iodination, as described in Example II, yields the desired product (18A).

EXAMPLE XVII

Reaction (18A)→(18B):

In a corresponding manner as described in Example III the above reaction is performed, resulting in the desired product (18B).

EXAMPLE XVIII

Reaction (14)→(46) as shown in Scheme H.

The reaction steps described in this Example are indicated with the numbers of the compounds as used in Scheme H.

(a) Reduction of the lactone functionality of compound (14) with diisobutylaluminium hydride (DIBAL-H) affords the 18-hydroxylated compound (38): THF/toluene (1.5:1), −78° C., DIBAL-H (3.5 equiv.), 15 min; −78° C.→room temp., yield 99%.

$^1$H-NMR ($CDCl_3$,δ): 0.95 (d, J=6.11 Hz, 3-H, $CH_3$-21), 1.21 (s, 6H, $CH_3$-26,27), 3.36 (s, 3H, $CH_3O$), 3.64 (d, J=11.8 Hz, 1H, CHHOH), 3.72 (d, J=11.9 Hz, 1H, CHHOH), 4.11 (s, 1H, H-8), 4.70 (s, 2H, $OCH_2O$). $^{13}$C-NMR ($CDCl_3$,δ): 18.50, 19.22, 20.27, 22.67,26.24, 26.33, 27.67, 33.78, 35.28, 36.37, 38.31, 42.22, 45.84, 52.96, 55.02, 57.33, 62.80, 68.08, 77.51, 90.99.

(b) Selective protection of the C-18 hydroxy group of cpd.(38) with tert-butyldimethylsilyl chloride gives cpd. (39): DMF, TBSCI (1.1 equiv.), imidazole (1.8 equiv.), cpd.(38) in $CH_2Cl_2$, room temp., 1 h, yield 76%.

$^1$H-NMR ($CDCl_3$,δ): 0.12 (s, 6H, $CH_3Si$), 0.93 (s, 9H, $Me_3CSi$), 0.95 (d, J=4.77 Hz, 3H, $CH_3$-21), 1.21 (s, 6H, $CH_3$-26,27), 3.36 (s, 3H, $OCH_3$), 3.63 (d, J=10.8 Hz, 1H, CHHOTBS), 3.71 (d, J=11.01 Hz, 1H, CHNOTBS), 3.90 (s, 1H, H-8), 4.70 (s, 2H, $OCH_2O$).

$^{13}$C-NMR ($CDCl_3$, δ): −5.86, −5.74, 18.21, 18.68, 18.92, 20.28, 22.69, 25.87, 26.28, 26.34, 27.68, 34.08, 35.44, 36.40, 38.17, 42.27, 45.82, 53.41, 55.03, 57.45, 63,75, 67.73, 76.30, 91.02.

(c) Oxidation of silylether (39) with pyridinium dichromate (PDC) gives ketone (40): $CH_2Cl_2$, 0° C., PDC (2.7 equiv.), PPTS (pyridinium p-toluene sulphonate; trace), 1 h; room temp., 4 h, yield 87%.

$^1$H-NMR ($CDCl_3$, δ): 0.01 (s, 6H, $CH_3Si$), 0.86 (s, 9H, $Me_3Si$), 1.02 (d, J=5.75 Hz, 3H, $CH_3$-21), 1.21 (s, 6H, $CH_3$-26,27), 3.34 (d, J=10.8 Hz, 1H, CHHOTBS), 3.49 (d, J=11.01 Hz, 1H, CHHOTBS), 3.36 (s, 3H, $OCH_3$), 4.70 (s, 2H, $OCH_2O$).

$^{13}$C-NMR ($CDCl_3$,δ): 18.20, 19.19, 19.32, 20.25, 23.81, 25.79, 26.27, 26.37, 27.53, 35.35, 35.80, 36.39, 40.54, 42.21, 53.39, 55.03, 56.89, 60.21, 61.78, 76.27, 91.03, 211.22.

EM [70 eV, m/z (%)]: 439 ($M^+$-$CH_3$, 0.92), 392 ($M^+$—$HOCH_2OCH_3$, 0.03), 335 (100), 225 (37.19), 149 (8.65), 119 (8.86).

(d) Ketone (40) serves as a common intermediate for the synthesis of both vitamin D analogues (49), according to Scheme J, and (46). The vinyl triflate (41) is prepared by treatment of cpd.(40) with LDA and trapping of the resulting kinetic enolate with N-phenyltriflimide: LDA (1.6 equiv.), THF, −78° C., cpd.(15) in THF, $PhNTf_2$ (2 equiv.) in THF, 2 h, −78° C. room temp. (slowly); yield 82% [plus 14% cpd.(40)]. $^1$H-NMR ($CDCl_3$, δ): 0.03 (s, 6H, $CH_3Si$), 0.88 (s, 9H, $Me_3CSi$), 1.04 (d, J=5.75 Hz, 3H, $CH_3$-21), 1.21 (s, 6H, $CH_3$-26,27), 3.36 (s,3H, $OCH_3$), 3.49 (s, 2H, $CH_2OTBS$), 4.70 (s, 2H, $OCH_2O$), 5.64 (dd, J=3.38, 6.75 Hz, 1H, H-9).

$^{13}$C-NMR ($CDCl_3$,δ): 18.13, 19.15, 20.25, 21.39, 23.99, 25.78, 26.29, 26.41, 28.19, 30.44, 35.69, 36.27, 42.15, 49.21, 49.58, 54.96, 55.03, 60.03, 76.30, 91.02, 117.22, 121.20, 149.23.

(e) Synthon (42) is obtained in 68% yield from the corresponding tertbutyldimethylsilyl-protected enyne by deprotection (n-Bu$_4$NF, THF) and reprotection (MOMCl, i-Pr$_2$NEt).

$^1$H-NMR (CDCl$_3$,δ): 1.68–1.80 (m, 1H, C$_2$HH), 2.00 (s, 3H, CH$_3$-19), 2.12–2.25 (m, 1H, CH$_2$-4), 2.55–2.64 (m, 1H, C$_2$HH), 3.10 (a, 1H, HCC), 3.38 (s, 3H, CH$_3$O), 3.44 (s, 3H, CH$_3$O), 3.93–4.04 (m, 1H, H-3), 4.12 (t, J=3.96 Hz, 1H, H-1).

$^{13}$C-NMR (CDCl$_3$,δ): 18.79, 34.67, 36.41, 55.70, 55.75, 69.09, 74.98, 80.43, 83.17, 95.22, 96.16, 115.73, 141.33.

Palladium-catalyzed assembly of both synthons (41) and (42) affords dienyne (43): DMF, Et$_3$N (3 equiv.), cpd.(42) (1 equiv.), (Ph$_3$P)$_2$PdCl$_2$ (0.04 equiv.), 70–75° C., 75 min; yield 74%.

$^1$H-NMR (CDCl$_3$,δ): 0.03 (s, 6H, CH$_3$Si), 0.89 (s, 9H, Me$_3$CSi), 1.05 (d, J=5.75 Hz, 3H, CH$_3$-21), 1.22 (s, 6H, CH$_3$-26,27), 3.38, 3.38 (ss, 6H, OCH$_3$), 3.43 (s, 3H, OCH$_3$), 3.45 (s, 2H, CH$_2$OTBS), 3.98 (m, 1H, H-3), 4.11 (m, 1H, H-1), 4.70, 4.71 (ss, 2H, OCH$_2$O), 4.72 (s, 2H, OCH$_2$O), 6.05 (d, J=3 Hz, 1H, H-9).

(f) Dienyne (43) is converted to the previtamin (44) by partial hydrogenation in the presence of Lindlar catalyst: Hexane, Lindlar cat., quinoline, H$_2$, room temp., 15 min; yield 93%.

(g) The previtamin is thermally equilibrated to a mixture of vitamin (45) and previtamin (44): Isooctane, 100° C., 5 h, ratio (45):(44)=85:15; yield 97%.

$^1$H-NMR (CDCl$_3$, δ): 0.01 (s, 6H, CH$_3$Si), 0.86 (s, 9H, Me$_3$CSi), 1.02 (d, J=5.75 Hz, 3H, CH$_3$-21), 1.21 (s, 6H, CH$_3$-26,27), 3.29 (a, 2H, CH$_2$OTBS), 3.36–3.45 (m, 9H, 3CH$_3$O), 4.06 (m, 1H, H-3), 4.28 (m, 1H, H-1), 4.6 (AB, J=6.65 Hz, 2H, OCH$_2$O), 4.70, 4.71 (2s, 4H, OCH$_2$O), 5.05 (s, 1H, H$_1$,), 5.28 (s, 1H, H,), 5.96, 6.35 (AB, J=10.70 Hz, 2H, H-6,7).

EM [70 eV, m/z (%)]: 678 (M$^+$, 2.04), 618 (2.09), 439 (5.65), 395 (6.54), 281 (7.05), 208 (9.37), 119 (23.61), 103 (44.81), 45 (100).

(h) This mixture is subsequently subjected to deprotection with AG 50W-X4® cation-exchange resin in methanol, to provide, after HPLC separation, the desired vitamin D analogue (46): AG 50W-X4, MeOH, room temp., 6 days in the dark; yield of prod.(46) 41%.

$^1$H-NMR (CDCl$_3$, δ): 1.10 (d, J=6.35 Hz, 3H, CH$_3$-21), 1.19 (s, 6H, CH$_3$-26,27), 3.41 (d, J=5.11 Hz, 2H, CH$_2$OH), 4.14 (m, 1H, H-3), 4.37 (m, 1H, H-1), 5.30 (s, 1H, H$_{19E}$), 6.09, 6.35 (AB, J=11.1 Hz, 2H, H-6,7). $^{13}$C-NMR (CDCl$_3$, δ): 19.94, 21.69, 23.05, 24.54, 28.54, 29.11, 29.28, 30.02, 36.46, 37.18, 37.91, 43.75, 45.36, 46.26, 50.92, 56.81, 58.46, 60.27, 67.40, 71.54, 71.68, 112.28, 119.20, 124.80, 136.13, 142.53, 149.83.

EXAMPLE XIX

Reaction (40)→(49) as shown in Scheme J.

(a) The reaction steps described in this Example are indicated with the numbers of the compounds as used in Scheme J.

Reaction of cpd.(40) with phosphine oxide anion (47) affords the protected vitamin D compound (48): 3 equiv. cpd.(47), THF, −78° C., cpd.(40) in THF, 1 h; −78°→room temp.; yield 87%.

$^1$H-NMR (CDCl$_3$, δ): 0.01 (s, 6H, Me$_2$Si), 0.71 (s, 6H, Me$_2$Si), 0.86 (s, 9H, Me$_3$CSi), 0.88 (s, 9H, Me$_3$CSi), 1.01 (d, J=6.3 Hz, 3H, CH$_3$-21), 1.21 (s, 6H, CH$_3$-26,27), 3.34 (s, 2H, CH$_2$OTBS), 3.36 (s, 3H, CH$_3$0), 3.81 (m, 1H, H-3), 4.70 (s, 2H, OCH$_2$O), 4.76 (s, 1H, H$_{192}$), 5.00 (s, 1H, H$_{19E}$), 5.98, 6.14 (AB, J=11.2 Hz, 2H, H-6,7).

$^{13}$C-NMR (CDCl$_3$, δ): −5.29, −4.63, 0.93, 15.19, 18.11, 19.31, 20.31, 22.20, 23.45, 25.82, 26.30, 26.43, 27.85, 28.93, 32.02, 32,64, 35.72, 36.33, 36.47, 42.16, 46.81, 49.75, 55.01, 55.44, 57.10, 60.78, 65.80, 70.60, 76.36, 91.01, 111.98, 118.15, 121.38, 136.56, 141.14, 145.66.

(b) Deprotection as described in Example XVIII [cpd. (45)→(46)] gives the desired vitamin D analogue (49) in 35% yield.

EXAMPLE XX

Biological experiments in vitro

Vitamin D analogue (46), prepared as described in Example XVIII, is dissolved in ethanol in concentrations ranging from $10^{-13}$ to $10^{-7}$ M. The affinity towards the calf thymus intracellular vitamin D receptor (VDR) is determined in a biological assay. In this assay $^3$H-calcitriol (1α,25-dihydroxycholecalciferol), which is specifically bound to the VDR, is replaced by the tested compound. The IC50 value, i.e. 50% replacement of $^3$H-calcitriol, is determined to be $2.5 \times 10^{-10}$ M. This indicates, that the tested compound has a high affinity to the VDR and consequently is a promising biologically active substance.

EXAMPLE XXI

Preparation of 1-(1,1-ethylenedioxy)ethyl-hydrindanol-4 [compound (2)]

Reaction (1)→(2) of Scheme A.

(a) The starting compound (1), viz. 7-dehydroprogesterone-3,20-diketal, in a quantity of 100 g is suspended into 1760 ml methanol and 88 ml dry pyridine. After cooling down to −75° C. under N$_2$ and while stirring, this suspension is flushed with ozone during 9.5 hr.

(b) The intermediate hydrindanone-4 is not isolated, but directly reduced by adding 24.8 g NaBH$_4$ to the above reaction mixture and stirring overnight at −75° C. Then another portion of 12.4 g NaBH$_4$ is added at 75° C. and the reaction mixture is allowed to warm up to −40° C. Stirring overnight at room temp. Another portion of 12.4 g NaBH$_4$ is added and the reaction mixture is stirred without external cooling for 1.5 hr. After evaporation at reduced pressure, the residue is taken up in a mixture of 400 ml saturated NaCl-solution, 200 ml water and 300 ml diethylether. The layers are separated and the aqueous layer is extracted twice with 200 ml diethylether. The combined ether layers are washed twice with 100 ml NaCl-solution, dried and evaporated to dryness. The desired hydrindanol compound (2) is obtained as a slightly yellow oil in a yield of 75.1 g. The product is subjected to flash chromatography: silicagel/ ethylacetate. The pure product (approx. 97% pure according to NMR) is obtained as a colourless oil. (88%; Rf: 0.43, 25% EtOAc/hexane; colourless oil).

$^1$H NMR (CDCl$_3$, δ) 4.05 (1H,m,H-8), 3.99–3.80(4H, m, OCH$_2$CH$_2$O), 2.02 (1H, m, H-17), 1.26 (3 H, s, Me-21), 1.00 (3 H, a, Me-17).

(c) In an alternative manner, hydrindanol compound (2) is prepared from starting compound (1) by a permanganate oxidation to the corresponding 7,8-diol compound, followed by an oxidation by lead tetra-acetate and a reduction: Aqueous KMnO$_4$ solution is added to solution of starting compound (1) in 96% ethanol at −20° C. Reaction time approx. 2 hrs. Further processing: filtration over filter aid and evaporation to dryness. Pb(OAc)$_4$ is added in portions to the diol, dissolved in dry dichloromethane, under $N_2$ at −10° C. Reaction time approx. 1 hr. Further processing: filtration over filter aid. Reduction by Red-Al® [sodium (bis-methoxyethoxyaluminiumhydride], dissolved in toluene. Reaction time approx. 0.5 hr at −5° C.→room temp. Preparation procedure: filtration and chromatographical purification (silicagel: ethylacetate/petroleum ether). The desired hydrindanol compound (2) is obtained in a high purity (NMR).

EXAMPLE XXII: (17)→(55). as shown in Scheme K

The reaction steps described in this Example are indicated with the numbers of the compounds as used in Scheme K.

(a) Reaction (17) (50): Compound (17), obtained according to Example X, is oxidized to compound (50) in a corresponding manner as described in Example XVIII (c) as follows:

Compound (17) (661 mg) is dissolved under argon in 40 ml dichloromethane and cooled to 0° C. PDC (2.002 g) is added and the reaction mixture is stirred at this temp. for 30 min., followed by stirring at room temp. for 38 h. Concentration under dim. pressure and column chromatography (silicagel; 15% EtOAc/hexane) yields 613 mg (93%) of the desired product.

$^1$H-NMR ($CD_2Cl_2$, δ): 0.93 (d, J=6.7 Hz, 3H, $CH_3$-21), 1.15 (s, 6H, $CH_3$-26,27), 3.28 (5, 3H, $OCH_3$), 4.62 (s, 2H, $OCH_2O$), 5.08 (m, 2H, $CH_2$=), 5.51 (dd, J=9.6, 18.6 Hz, 1H, CH=).

$^{13}$C-NMR ($CD_2Cl_2$, δ): 18.65, 19.42, 20.72, 23.87, 26.47, 26.53, 27.86, 35.69, 36.13, 36.50, 40.87, 42.60, 55.15, 56.80, 58.15, 61.73, 76.41, 91.36, 116.97, 136.63, 211.09.

(b) Reaction (50)→(51) is performed in a corresponding manner as described in Example XVIII (d) as follows:

$iPr_2NH$ (0.834 ml, 3.998 mmoles) is added dropwise to 2.35 M (1.685 ml) nBuLi under argon at −80° C. After adding 4 ml dry THF, the solution is allowed to reach 0° C. and stirred at this temp. for 30 min. After cooling to −80° C., an equimolar quantity of $PhNTf_2$ in THF is added, after which the reaction mixture is quenched with a few drops of MeOH after having reached room temp. Concentration at dim. pressure and column chromatography (silicagel; 5–20% EtOAc/hexane) yields 104 mg (66%) of the desired product.

$^1$H-NMR ($CDCl_3$, δ): 0.92 (d, J=5.95 Hz, 3H, $CH_3$-21), 1.20 (s, 6H, $CH_3$-26,27), 3.36 (s, 3H, $OCH_3$), 4.70 (s, 2H, $OCH_2O$), 5.19 (m,2H, $CH_2$=), 5.49 (dd, J=3.36, 6.78 Hz, 1H, H-9), 5.67 (m, 1H, $C_{18}H$=). $^{13}$C-NMR ($CDCl_3$,δ): 18.09, 20.39, 21.03, 23.91, 26.26, 26.33, 28.19, 31.41, 35.74, 36.04, 42.26, 49.90, 52.61, 55.03, 55.12, 76.28, 91.03, 116.01, 116.75, 134.63, 149.41.

(c) Reaction (51)→(52) is performed in a corresponding manner as described in Example XVIII (e) as follows:

The triflate (51) in an amount of 107 mg, 96 mg of the enyne, 6 mg of $Pd(Ph_3P)_2Cl_2$ as a catalyst and 0.065 ml TEA are dissolved into 2 ml DMF. The solution is stirred under argon at 70–75° C. for 1 h 15 min. The reaction mixture is concentrated under reduced pressure and the residue is chromatographed (silicagel; 5–10% EtOAc/hexane), yielding 115 mg (73%) of the desired dienyne (52).

$^1$H-NMR ($CDCl_3$, δ): 0.03 (5, 6H, $CH_3Si$), 0.89 (8, 9H, $Me_3CSi$), 1.05 (d, J=5.75 Hz, 3H, $CH_3$-21), 1.22 (s, 6H, $CH_3$-26,27), 3.38, 3.38 (ss, 6H, $OCH_3$), 3.43 (s, 3H, $OCH_3$), 3.45 (s, 2H, $CH_2OTBS$), 3.98 (m, 1H, H-3), 4.11 (m, 1H, H-1), 4.70, 4.71 (ss, 2H, $OCH_2O$), 4.72 (s, 2H, $OCH_2O$), 6.05 (d, J=3 Hz, 1H, H-9).

(d) Reaction (52)→(53) is performed in a corresponding manner as described in Example XVIII (f) as follows: The dienyne (52) (45 mg) is dissolved into 6 ml hexane. A solution of quinoline in hexane (0.115 ml; solution of 0.060 ml quinolein in 10 ml hexane) and 50 mg of Lindlar catalyst are added. The reaction mixture is flushed with hydrogen, filtered over celite and concentrated. Purification by column chromatography (silicagel; 5–10% EtOAc/hexane) yields 43 mg (96%) of previtamin compound (53).

(e) Reaction (53)→(54) is performed in a corresponding manner as described in Example XVIII (g) as follows: The previtamin (53) (40 mg) is dissolved into 4 ml iso-octane and heated at 110° C. for 5 h under argon. Concentration under red. pressure and column chromatography yields 38 mg (92%) of the desired vitamin D compound (54).

(f) Reaction (54)→(55) is performed in a corresponding manner as described in Example XVIII (h) as follows:

The vitamin compound (54) in an amount of 40 mg, dissolved in 10 ml MeOH, is stirred with 2 g resin AG 50W-X4® for 18 h under argon and shielded from the light. After filtration, washing with EtOAc (4×10 ml) and concentration under red. pressure, the product obtained is chromatographed: silicagel; 50% EtOAc/hexane, EtOAc. The desired 18-vinyl modified 1α,25-dihydroxyvitamin $D_3$ (55) is obtained in a yield of 13 mg.

$^1$H-NMR ($CD_2Cl_2$, δ): 0.88 (d, J=5.96 Hz, 3H, $CH_3$-21), 1.13 (s, 6H, $CH_3$-26,27), 4.09 (m, 1H, H-3), 4.35 (m, 1H, H-1), 4.93 (s, 1H, H-19E), 5.06 (ABX, J=11.3, 17.8 Hz, 2H, $C_2$=), 5.27 (s, 1H, H-19Z), 5.43 (ABX, J=11.4, 17.8 Hz, 1H, CH=), 6.02, 6.28 (AB, J=11.26 Hz, 2H, H-6,7). $^{13}$C-NMR ($CD_2Cl_2$,δ): 18.45, 21.16, 22.15, 23.88, 27.87, 29.38, 29.51, 36.26, 36.58, 37.02, 43.46, 44.89, 45.79, 56.82, 57.98, 67.16, 71.14, 71.23, 111.90, 115.73, 116.79, 124.96, 134.28, 137.63, 142.93, 148.62.

EXAMPLE XXIII; (17)—(58), as shown in Scheme K (a) Reaction (17)→(56):

Compound (17), obtained according to Example X, in an amount of 124 mg is dissolved into 10 ml of dry EtOH. In the presence of 40 mg 5% Pt/C as a catalyst the hydrogenation at a hydrogen pressure of 35 psi is carried out at room temp. while stirring for 21 h. The solution is filtered over celite, concentrated under dim. pressure and chromatographed (silicagel; 15% EtOAc/hexane), to yield 121 mg (97%) of the desired product (56). $^1$H-NMR ($CDCl_3$,δ): 0.91 (t, J=7.6 Hz, 3H, $CH_3$-18), 0.98 (d, J=6.7 Hz, 3H, $CH_3$-21), 1.22 (s, 6H, $CH_3$-26,27), 3.37 (s, 3H, $OCH_3$), 4.10 (s, 1H, H-8), 4.71 (s, 2H, $OCH_2O$).

$^{13}$C-NMR ($CDCl_3$,δ): 10.14, 17.57, 19.02, 19.52, 20.34, 22.04, 26.27, 26.34, 26.83, 33.78, 34.82, 36.47, 36.71, 42.31, 44.48, 53.62, 55.00, 58.45, 69.62, 76.35, 91.01.

(b) Reaction (56)→(57) is performed in a corresponding manner as described in Example XXII (a).

$^1$H-NMR: ($CD_2Cl_2$, δ): 0.87 (m, 3H, $CH_3$-18), 1.01 (d, J=6.19 Hz, 3H, $CH_3$-21), 1.16 (s, 6H, $CH_3$-26,27), 3.29 (s, 3H, $OCH_3$), 4.63 (s, 2H, $OCH_2O$).

(c) Reaction sequence (57)→(58) is carried out in a corresponding manner as described in Examples XXII (b) to XXII (f).

Physical data:

triflate, compound (51)-analogue, wherein $R_3$=ethyl:

$^1$H-NMR ($CDCl_3$, δ): 0.97 (m, 3H, $CH_3$-18), 1.01 (d, J=6.19 Hz, 3 H, $CH_3$-21), 1.21 (s, 6H, $CH_3$-26,27), 3.37 (s, 3H, $OCR_3$), 4.71 (8, 2H, $OCH_2O$), 5.61 (dd, J=3.29, 6.57 Hz, 1H, H-9).

$^{13}$C-NMR ($CDCl_3$, δ): 10.19, 18.68, 19.33, 20.29, 20.68, 24.16, 26.32, 27.68, 31.34, 35.23, 36.39, 42.30, 47.51, 51.44, 55.03, 56.38, 76.27, 91.04, 116.45, 150.02.

coupling product, compound (52)-analogue, wherein $R_3$-ethyl:

$^1$H-NMR (CD$_2$Cl$_2$, δ): 0.03 (s, 6H, Me$_2$Si), 0.07 (s, 6H, Me$_2$Si), 0.85 (s, 9H, Me$_3$CSi), 0.87 (s, 9H, Me$_3$CSi), 0.93 (t, J=7.23 Hz, 3H, CH$_3$-18), 0.99 (d, J=6.38 Hz, 3H, CH$_3$-21), 1.15 (s, 6H, CH$_3$-26,27), 3.28 (s, 3H, OCH$_3$), 4.06 (m, 1H, H-1), 4.62 (s, 2H, OCH$_2$O), 5.95 (m, 1H, H-9). $^{13}$C-NMR (CD$_2$Cl$_2$, δ): −4.71, −4.59, −4.54, −4.25, 10.74, 18.28, 18.36, 18.84, 19.27, 19.66, 20.75, 24.00, 25.87, 25.99, 26.04, 26.53, 27.82, 32.94, 35.91, 36.96, 40.26, 41.66, 42.73, 44.68, 51.89, 55.15, 57.22, 64.74, 70.44, 76.47, 88.54, 91.40, 93.01, 115.98, 123.22, 134,26, 140.88.

vitamin D$_3$ derivative, compound (55)-analogue, wherein R$_3$=ethyl:

$^1$H-NMR (CD$_2$Cl$_2$, δ): 0.81 (t, J=7.29 Hz, 3H, CH$_3$-18), 0.98 (d, J=6.14 Hz, 3H, CH$_3$-21), 1.14 (s, 6H, CH$_3$-26,27), 4.12 (m, 1H, H-3), 4.12 (m, 1H, H-1), 4.92 (s, 1H, H-19E), 5.26 (s, 1H, H-19Z), 5.98, 6.33 (AB, J=11.26 Hz, 2H, H-6,7).

$^{13}$C-NMR (CD$_2$Cl$_2$, δ) 9.52, 15.48, 18.52, 19.86, 21.10, 21.96, 24.21, 27.38, 29.43, 29.56, 35.67, 36.78, 36.97, 43.50, 44.97, 45.87, 48.29, 58.00, 58.82, 67.21, 71.17, 71.29, 111.92, 118.15, 125.05, 134.07, 143.80, 148.63.

EXAMPLE XXIV

Reaction sequence (7)→(13) as shown in Scheme A "alt."

(a) The alternative ("alt.") oxidation of (7)→(9) is performed as follows:

A stirred suspension of Pb(OAc)$_4$ (43.6 g) and CaCO$_3$ (8.27 g) in dry cyclohexane (350 ml) is heated to 80° C. The starting compound (7) (5.00 g) and iodine (6.50 g) are successively added, after which the reaction mixture is heated and irradiated with a 300 watt tungsten lamp for 3 h.

After cooling to room temp., the reaction mixture is filtered and washed with Et$_2$O. The filtrate is washed with 5% Na$_2$S$_2$O$_3$ solution and water. A drop of pyridine is added to the organic layer after separation thereof. Drying and concentration gives a residue which is dissolved in acetone. The solution is cooled to 0° C. and 10 ml of Jones reagent (13.3 g CrO and 11.5 ml conc. H$_2$SO$_4$ diluted with water to 50 ml) is added dropwise; the reaction mixture is stirred overnight. A solution of NaOAc (100 g) and water (200 ml) is added and the mixture is filtered. The aqueous phase is extracted with EtOAc, and the combined organic layers are washed with brine, dried, filtered and concentrated. Flash chromatography (5–10% EtOAc/hexane) yields 3.8 g (72%) of compound (9).

$^1$H-NMRδ: 1.18 (d, J=6.7 Hz, 3H, CH$_3$-21), 2.06 (s, 3H, OCOCH$_3$), 3.89 (dd, J=6.3, 10.8 Hz, 1H, H-22), 4.07 (dd, J=3.5, 10.8 Hz, 1H, H-22), 4.6 (d, J=4.7 Hz, 1H, H-8).

(b) Reaction sequence (9)→(13) of Scheme A "alt.".

(b-i): conversion of the acetate group into a hydroxy group. A solution of compound (9) in methanol is stirred at room temp. in the presence of K$_2$CO$_3$ for 45 min. Addition of water, extraction with Et$_2$O and working-up procedure yields the corresponding hydroxy compound, after flash chromatography, in a yield of 95%. $^1$H-NMR δ: 1.19 (d, J=6.7 Hz, 3H, CH$_3$-21), 3.48 (m, 1H, H-22), 3.65 (m, 1H, H-22), 4.58 (d, J=4.6 Hz, 1H, H-8).

(b-ii): conversion of the hydroxy group into a iodo substituent.

The above hydroxy compound is treated with iodine in the presence of PPh$_3$ and imidazole in dry THF at −7° C. for 15 min. Evaporation, addition of NaHCO$_3$, extraction with Et$_2$O and working-up gives the desired iodo compound after flash chromatography (5–10% EtOAc/hexane) in a yield of 96%. $^1$H-NMR δ: 1.15 (d, J=6.2 Hz, 3H, CH$_3$-21), 3.32 (m, 2H, H-22), 4.58 (d, J=4.7 Hz, 1H, H-8).

(b-iii): conversion with methyl vinyl ketone.

The obtained iodo compound is treated with methyl vinyl ketone under sonication in deoxygenated EtOH/H$_2$O in the presence of Zn dust and CuI: 30 min. at room temp. under argon. Addition of Et$_2$O and filtration. The filtrate is worked up and submitted to flash chromatography (5–10% EtOAc/hexane), yielding 88% of the desired 25-oxo-27-nor-lactone compound. $^1$H-NMR δ: 1.09 (d, J=6.6 Hz, 3H, CH$_3$-21), 1.57 or 2.13 (s, 3H, CH$_3$-26), 4.56 (d, J=4.5 Hz, 1H, H-8).

(b-iv): conversion to compound (13).

The above-obtained compound is treated with MeLi in dry Eto at −4° C. for 5 min. Quenching with water, and working-up of the organic phase gives a product, which after flash chromatography (10–20% EtOAc/hexane) yields compound (13) in a yield of 87%. $^1$H-NMR δ: 1.10 (d, J=6.6 Hz, 3H, CH$_3$-21), 1.21 (s, 6H, CH$_3$-26,27), 4.55 (d, J=4.5 Hz, 1H, H-8).

(b-v): protection of the 25-hydroxy group.

The 25-hydroxy group can be protected by a reaction of the above-obtained compound with chlorotriethylsilane in the presence of triethylamine and 4-dimethylaminopyridine in dry CH$_2$Cl$_2$ at 0° C.: 1 h, followed by stirring at room temp for 20 h. Addition of water, extraction with CH$_2$Cl$_2$ and usual working up gives the trimethylsilyl ether of compound (13) in a yield of 87%. $^1$H-NMR δ: 0.54 [q, J=7.8 Hz, 6H, Si(CH$_2$Me)$_3$], 0.93 [t, 9H, J=7.8 Hz, Si(CCH$_3$)$_3$], 1.08 (d, 3H, J=6.5 Hz, CH$_3$-21), 1.17 (s, 6H, CH$_3$-26,27), 4.55 (d, 1H, J=4.5 Hz, H-8).

EXAMPLE XXV

Reaction sequence (9)→(70) as shown in Scheme L.

The reaction steps described in this Example are indicated again with the numbers of the compounds as used in the Scheme.

(a) Reaction (9)→(59): Compound (9), obtained as described in Example XIII, is converted to compound (59) in a corresponding manner as described in Example XXIV (b).

(b) Reaction (59)→(60):

Imidazole (95 mmoles) and t.-butyldimethylsilyl chloride (83.5 mmoles) are added to a stirred solution of 17.03 g of compound (59) in 200 ml DMF. After 20 hrs reaction at room temp., the reaction mixture is evaporated, and water and EtOAc/hexane are added. After separation, the organic layer is washed with 0.2 N HCl solution, 5% NaHCO$_3$ solution and satd. NaCl solution, dried and filtered. Concentration yields the desired product (25.86 g). Purification by crystallization from MeOH/EtOAc yields a crystalline material: m.p. 48–49° C.

$^1$H-NMR (CDCl$_3$,δ): 0.86 [s, 9H, SiC(CH$_3$)$_3$], 1.12 (d, 3H, CH$_3$-21), 2.31 (m, 1H, CH-14), 3.43 (dd, 1H, CH-22), 3.52 (dd, 1H, CH-22), 4.54 (d, 1H, CH-8).

(c) Reaction (60)→(61) is performed in a corresponding manner as described in Example XVIII (a). (d) Reaction (61)→(62) is performed in a corresponding manner as described in Example X. $^1$H-NMR (CDCl$_3$,δ): 0.86 [s, 9H, SiC(CH$_3$)$_3$], 0.88 (d, 3H, CH$_3$-21), 2.51 (m, 1H, CH-14), 3.28 (dd, 1H, CH-22), 3.49 (dd, 1H, CH-22), 3.93 (b, 1H, CH-8), 5.26 (m, 2H, =CH$_2$), 5.88 (m, 1H, —CH=C).

(e) Reaction (62)→(63):

An aqueous HF solution (94 mmoles) is added dropwise to a stirred solution of 17.61 g of compound (62) in acetonitrile. After 20 min at room temp. a 5% NaHCO$_3$ solution is added and the reaction mixture is stirred for an additional 10 min. The reaction mixture is poured into a satd. NaCl solution and extracted with diethylether (3x). After washing with satd. NaCl solution, the organic phase is dried, filtered and concentrated under red. pressure, yielding the desired compound (12.04 g). $^1$H-NMR (CDCl$_3$,δ): 0.96 (d, 3H, CH$_3$-21), 2.53 (dt, 1H, CH-14), 3.39 (dd, 1H, CH-22), 3.58 (d, 1H, CH-22), 3.96 (b, 1H, CH-8), 5.29 (m, 2H, =CH$_2$), 5.99 (m, 1H, CH=C).

(f) Reaction (63)→(64):

Pd/C 10% (500 mg) as a catalyst is added to a solution of 11.60 g of compound (63) in MeOH. The reaction mixture is hydrogenated in a Parr apparatus for 17 hours (pressure approx. 3.5 bar). The reaction mixture is filtered over celite, concentrated under red. pressure and chromatographed over silicagel (petr.ether/EtOAc—55/45), yielding 11.4 g of compound (64). $^1$H-NMR (CDCl$_3$, δ): 0.92 (t, 3H, CH$_3$-18), 1.11 (d, 3H, CH$_3$-21), 2.31 (dt, 1H, CH-14), 3.40 (m, 1H, CH-22), 3.65 (m, 1H, CH-22), 4.11 (b, 1H, CH-8).

(g) Reaction (64)→(18A) is performed in a corresponding manner as described in Example XXIV (b). $^1$H-NMR (CDCl$_3$, δ): 0.91 (t, 3H, CH$_3$-18), 1.08 (d, 3H, CH$_3$-21), 2.26 (m, 1H, CH-14), 3.23 (dd, 1H, CH-22), 3.33 (dd, 1H, CH-22), 4.12 (b, 1H, CH-8).

(h) Reaction (18A)→(65) is performed in a corresponding manner as described in Example XVIII (c). $^1$H-NMR (CDCl$_3$, δ): 0.89 (t, 3H, CH$_3$-18), 1.13 (d, 3H, CH$_3$-21), 2.49 (m, 1H, CH-14), 3.23 (dd, 1H, CH-22), 3.32 (dd, 1H, CH-22).

(i) Reaction (65)→(66) is performed in a corresponding manner as described in Example XVIII (d).$^1$ H-NMR (CDCl$_3$,δ): 0.97 (t, 3H, CH$_3$-18), 1.11 (d, 3H, CH$_3$-21), 2.58 (m, 1H, CH-14), 3.21 (dd, 1H, CH-22), 3.32 (dd, 1H, CH-22), 5.63 (q, 1H, CH-9).

(j) Reaction (66)→(67) is performed in a corresponding manner as described in Example III. $^1$H-NMR (CDCl$_3$, δ): 0.96 (t, 3H, CH$_3$-18), 1.02 (d, 3H, CH$_3$-21), 1.26 (t, 3H, OCCH$_3$), 2.51 (m, 1H, CH-14), 4.13 (q, 2H, OCH$_2$C), 5.61 (q, 1H, CH-9).

(k) Reaction (67)→(68) is performed in a corresponding manner as described in Example XXII (c) $^1$H-NMR (CDCl$_3$, δ): 0.06 (s, 6H, SiMe$_2$), 0.09 (s, 6H, SiMe$_2$), 0.88 [2xs, 2x9H, 2xSiC(CH$_3$)$_3$], 0.94 (t, 3H, CH$_3$-18), 1.02 (d, 3H, CH$_3$-21), 1.26 (t, 3H, OCCH$_3$), 1.89 (b, 3H, CH$_3$-19), 2.40 (m, 1H, CH-14), 4.09 (b, 1H, CH-3), 4.13 (q, 2H, OCH$_2$C), 4.19 (b, 1H, CH-1), 6.01 (b, 1H, CH-9).

(l) Reaction (68)→(69) is performed in a corresponding manner as described in Example XXII (d).

(m) Reaction (69)→(70) is performed in a corresponding manner as described in Example XXII (e). $^1$H-NMR (CDCl$_3$, δ): 0.06 (s, 6H, SiMe$_2$), 0.09 (s, 6H, SiMe$_2$), 0.88 [s, 18H, 2xSiC(CH$_3$)$_3$], 0.89 (t, 3H, CH$_3$-18), 1.01 (d, 3H, CH$_3$-21), 1.26 (t, 3H, OCCH$_3$), 2.45 (m, 1H, CH-14), 4.13 (q, 2H, OCH$_2$C), 4.37 (m, 1H, CH-1), 4.19 (m, 1H, CH-3), 4.86 (b, 1H, CH-19Z), 5.17 (b, 1H, CH-19E), 6.01 (d, 1H, CH-7), 6.24 (d, 1H, CH-6).

(n) Reaction (70)→(58) is performed by subjecting compound (70) to a conventional double Grignard reaction (MeMgX) or to a reaction with MeLi, followed by deprotection in a corresponding manner as described in Example XXII (f). So the desired C-18 modified 1α,25-dihydroxyvitamin D$_3$ compound (58) is obtained.

EXAMPLE XXVI

Reaction sequence (71)→(74) as shown in Scheme N.

The reaction steps described in this Example are again indicated with the numbers of the compounds as used in the Scheme.

(a) Reaction (71)→(72):

Compound (71), prepared from vitamin D$_3$ in a corresponding manner as described in Example I, is converted to compound (72) in a corresponding manner as described in Example IV. $^1$H-NMR (CDCl$_3$,δ): 0.86 (dd, 6H, CH-26,27), 0.88 (d, 3H, CH$_3$-21), 2.06 (dd, 1H, CH-14), 3.72 (m, 2H, OCH$_2$-C18), 4.14 (d, 1H, CH-8).

(b) Reaction (72)→(13):

RuO$_2$.xH$_2$O (0.01 mol) and NaIO$_4$ (0.606 mol) are stirred in water. To this mixture is added 26.62 g of compound (72), dissolved in EtOAc. The reaction mixture is stirred vigorously at 60° C. for 3 h 45 min. Then diethylether and satd. NaCl solution are added and the reaction mixture is filtered over celite. After separation, the organic phase is washed with water and satd. NaCl solution, dried, filtered and concentrated under red. pressure. Purification by column chromatography (silicagel; petr.ether/EtOAc—93/7 70/30) yields 10.0 g of compound (13), in addition to intermediate (73) (9.0 g).

Compd. (73): $^1$H-NMR (CDCl$_3$, δ): 0.86 (dd, 6H, CH$_3$-26,27), 1.09 (d, 3H,CH$_3$-21), 2.36 (m, 1H, CH-14), 4.55 (d, 1H, CH-8).

Compd. (13): $^1$H-NMR (CDCl$_3$, δ): 1.09 (d, 3H, CH$_3$-21), 1.20 (d, CH$_3$-26,27), 2.35 (m, 1H, CH-14), 4.56 (d, 1H, CH-8).

(c) Reaction (13)→(74): Lutidine (2.6 g, 63.4 mmoles) and triethylsilyltriflate (39.6 mmoles) are added to a solution of 9.35 g of the above compound (13) in dry dichloromethane. After 30 min water is added. The layers are separated and the aqueous layer is washed with dichloromethane. The collected organic layers are dried, filtered and concentrated under red. pressure. The residue is purified by column chromatography (silicagel; petr.ether/EtoAc=95/5), yielding 13.16 g of compound (74).

$^1$H-NMR (CDCl$_3$, δ): 0.58 (q, 6H, 3xSiCH$_2$CH$_2$), 0.94 (m, 9H, 3xSiCCH$_3$), 1.09 (d, 3H, CH$_3$-21), 1.18 (d, 6H, CH$_3$-26,27), 2.37 (m, 1H, CH-14), 4.55 (d, 1H, CH-8).

We claim:

1. A vitamin D compound of the general formula

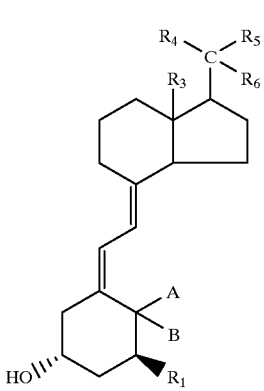

(I)

wherein

R$_1$ is a hydrogen atom or a hydroxy group;

R$_3$ is a C$_2$–C$_5$ alkyl group, $R_4$ is a hydrogen atom or a $C_1$–$C_4$ alkyl group;

$R_5$ is a branched or non-branched, saturated or unsaturated aliphatic hydrocarbyl or hydrocarbyloxy group, which comprises 1 to 16 carbon atoms and which is optionally substituted with one or more substituents, selected from hydroxy groups, ether groups, oxo functions, cyclopropyl groups, lactone groups and fluorine atoms;

R is a hydrogen atom or a $C_1$–$C_4$ alkyl group; and

A and B are each individually hydrogen atoms or methyl groups, or,

A and B form together a methylene group.

2. A method of preparing a vitamin D compound as claimed in claim 1, characterized in that a hydrindane compound of the general formula X:

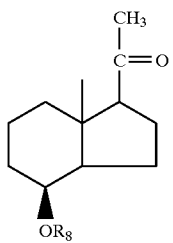
(X)

wherein $R_8$ is a hydroxy-protecting group; is converted to the corresponding cyanohydrin of the general formula XI

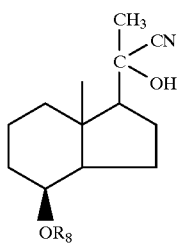
(XI)

wherein $R_8$ has the above meaning;

after which said cyanohydrin is converted to a hydrindane intermediate of the general formula XII

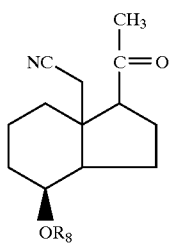
(XII)

which intermediate is subjected to a reaction sequence to produce, in a manner known per se for related compounds, substitutent $R_3$ in the 7a position and to convert substituent $CH_3O$ into substituent $R_4C(R_5)R_6$; after which the hydrindane compound obtained, having the general formula IX

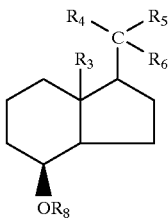
(IX)

wherein $R_3$, $R_4$, $R_5$ and $R_6$ are as defined in claim 1, is converted in a manner known per se for related compounds, either (a) with a Wittig reagent of the general formula V

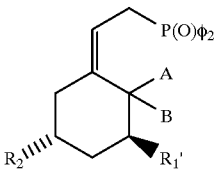
(V)

wherein:

$R_1$ is a hydrogen atom or a protected hydroxy group, $R_2$ is a protected hydroxy group, and A and B have the meanings given in claim 1, or (b), after enolization, with an enyne compound of the general formula VI

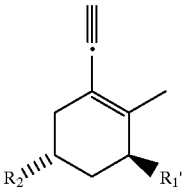
(VI)

where $R_1$ and $R_2$ have the above meanings, followed by hydrogenation and equilibration; into a vitamin D compound of the general formula I

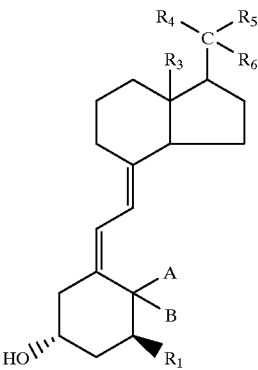
(I)

wherein the substituents $R_1$, $R_3$, $R_4$, $R_5$, $R_6$, A, and B are as defined in claim 1.

3. A vitamin D compound as claimed in claim 1, wherein $R_1$, $R_3$, A and B have the meanings given in claim 1, $R_4$ is a methyl group, $R_6$ is a hydrogen atom or a methyl group, and $R_5$ is an aliphatic hydrocarbyl group selected from the group consisting of 3,4-dimethylpenten-1-yl, 3,4-dimethyl-4-hydroxpenten-1-yl, 3-hydroxy-4-methylpentyl, 4-hydroxy-4-methylpentyl, 3,4-dihydroxy4-methylpentyl, 3,3-difluoro-4-hydroxy-4-methylpentyl, 3-methylbutoxy, 3-hydroxy-3-methylbutoxy, 3-cyclopropyl-3-hydroxypropen-1-yl and 3-cyclopropyl-3-hydroxy-3-3-methylpropen-1-yl; or its corresponding 24-homo-, 26-homo-24,24-dihomo-26,27-dihomo-24,26,27-trihomo- or 24,26,27-tetrahomo-vitamin D analogue.

* * * * *